(12) United States Patent
Liu et al.

(10) Patent No.: US 11,179,714 B2
(45) Date of Patent: Nov. 23, 2021

(54) IN-SITU PREPARATION METHOD FOR CATALYST FOR PREPARING AT LEAST ONE OF TOLUENE, PARA-XYLENE AND LIGHT OLEFINS, AND REACTION PROCESS

(71) Applicant: DALIAN INSTITUTE OF CHEMICAL PHYSICS, CHINESE ACADEMY OF SCIENCES, Liaoning (CN)

(72) Inventors: Zhongmin Liu, Liaoning (CN); Zhengxi Yu, Liaoning (CN); Shukui Zhu, Liaoning (CN); Yue Yang, Liaoning (CN)

(73) Assignee: DALIAN INSTITUTE OF CHEMICAL PHYSICS, CHINESE ACADEMY OF SCIENCES, Liaoning (CN)

( * ) Notice: Subject to any disclaimer, the term of this patent is extended or adjusted under 35 U.S.C. 154(b) by 164 days.

(21) Appl. No.: 16/608,818

(22) PCT Filed: Apr. 27, 2017

(86) PCT No.: PCT/CN2017/082222
§ 371 (c)(1),
(2) Date: Oct. 26, 2019

(87) PCT Pub. No.: WO2018/195865
PCT Pub. Date: Nov. 1, 2018

(65) Prior Publication Data
US 2020/0179917 A1   Jun. 11, 2020

(51) Int. Cl.
*C07C 1/22* (2006.01)
*B01J 37/02* (2006.01)
(Continued)

(52) U.S. Cl.
CPC .......... *B01J 37/0236* (2013.01); *B01J 29/40* (2013.01); *B01J 29/70* (2013.01); *B01J 29/85* (2013.01);
(Continued)

(58) Field of Classification Search
CPC ........ B01J 37/0236; B01J 29/40; B01J 29/70; B01J 29/85; B01J 37/04; B01J 2229/183;
(Continued)

(56) References Cited

U.S. PATENT DOCUMENTS 4,554,394 A * 11/1985 Forbus ................. B01J 29/40
585/474
4,950,835 A   8/1990 Wang et al.
(Continued)

FOREIGN PATENT DOCUMENTS

CN   1100402 A   3/1995
CN   1124950 A   6/1996
(Continued)

*Primary Examiner* — Thuan D Dang
(74) *Attorney, Agent, or Firm* — Seed IP Law Group LLP

(57) ABSTRACT

Disclosed is an in-situ preparation method for a catalyst for Reaction I: methanol and/or dimethyl ether with toluene are used to prepare light olefins and co-produce para-xylene and/or Reaction II: methanol and/or dimethyl ether with benzene are used to prepare at least one of toluene, para-xylene and light olefins, comprising: contacting at least one of a phosphorus reagent, a silylation reagent and water vapor with a molecular sieve in a reactor to prepare, in situ, the catalyst for the Reaction I and/or the Reaction II, wherein the reactor is a reactor of the Reaction I and/or the Reaction II. By directly preparing a catalyst in a reaction system, the entire chemical production process is simplified, the catalyst preparation and transfer steps are saved, and the operation thereof is easy. The catalyst prepared in situ can be directly used for in situ reactions.

13 Claims, 3 Drawing Sheets

(51) Int. Cl.
  *B01J 29/40* (2006.01)
  *B01J 29/70* (2006.01)
  *B01J 29/85* (2006.01)
  *B01J 37/04* (2006.01)
  *C07C 2/86* (2006.01)

(52) U.S. Cl.
  CPC .............. *B01J 37/04* (2013.01); *C07C 1/22* (2013.01); *C07C 2/86* (2013.01); *B01J 2229/183* (2013.01); *B01J 2229/34* (2013.01); *C07C 2529/40* (2013.01); *C07C 2529/70* (2013.01)

(58) Field of Classification Search
  CPC .... B01J 2229/34; B01J 37/10; B01J 2229/12; B01J 2229/186; B01J 2229/32; B01J 2229/40; B01J 37/0009; B01J 37/0018; B01J 37/0045; B01J 37/0036; B01J 37/009; B01J 37/0063; B01J 35/023; B01J 35/002; B01J 35/0006; B01J 37/08; B01J 23/00; B01J 8/02; B01J 29/06; B01J 37/00; C07C 1/22; C07C 2/86; C07C 2529/40; C07C 2529/70; C07C 1/20; C07C 2/865; C07C 2/864; C07C 11/02; C07C 15/08; C07C 7/20; Y02P 30/20; Y02P 30/40; Y02P 20/52
  See application file for complete search history.

(56) References Cited

U.S. PATENT DOCUMENTS 5,571,768 A * 11/1996 Chang ................. B01J 29/40
 502/64
2017/0152197 A1 6/2017 Xu et al.
2020/0179891 A1 6/2020 Zhang et al.
2020/0188869 A1 6/2020 Zhang et al.

FOREIGN PATENT DOCUMENTS

| CN | 105195213 A | 12/2015 |
|---|---|---|
| CN | 105272798 A | 1/2016 |
| CN | 105283415 A | 1/2016 |
| CN | 106588528 A | 4/2017 |
| KR | 10-2017-0013988 A | 2/2017 |

* cited by examiner

IN-SITU PREPARATION METHOD FOR CATALYST FOR PREPARING AT LEAST ONE OF TOLUENE, PARA-XYLENE AND LIGHT OLEFINS, AND REACTION PROCESS

TECHNICAL FIELD

The present application relates to an in-situ preparation method of a catalyst for preparing at least one of toluene, para-xylene and light olefins, and a reaction process for preparing at least one of toluene, para-xylene and light olefins, and belongs to the field of chemical engineering.

BACKGROUND

Ethylene and propylene are the cornerstones of the vast petrochemical industry, and most organic chemicals are derived from ethylene and propylene. Para-xylene (PX) is a raw material for producing polyesters such as PET (polyethylene terephthalate), PBT (polybutylene terephthalate) and PTT (polytrimethylene terephthalate). In recent years, the large number of applications of polyester in textile and garment, beverage packaging and other fields has driven the rapid growth of production and consumption of PTA (pure terephthalic acid) and upstream product PX. At present, the source of PX is mainly prepared by disproportionation, isomerization and adsorption separation or cryogenic separation using toluene, $C_9$ aromatic hydrocarbon and mixed xylene obtained by naphtha reforming, and the equipment investment is large and the operation cost is high. Since the content of para-xylene in the product is thermodynamically controlled, para-xylene only accounts for about 20% of the xylene isomer, and the difference among the boiling points of the three xylene isomers is small. Purity para-xylene cannot be obtained by ordinary distillation techniques, and must be obtained by an expensive adsorption separation process.

U.S. Pat. Nos. 3,911,041, 4,049,573, 4,100,219, et al. discloses the reaction of preparing olefins from methanol on phosphorus, magnesium and silicon modified HZSM-5 catalysts. The reaction of phosphorus, lanthanum modified HZSM-5 molecular sieve catalyst to obtain light olefins from methanol or dimethyl ether. U.S. Pat. Nos. 5,367,100 and 5,573,990 discloses the reaction of the Dalian Institute of Chemical Physics of the Chinese Academy of Sciences using phosphorus and lanthanum modified HZSM-5 molecular sieve catalysts to prepare light olefins from methanol or dimethyl ether. Since the 1970s, the research on the technology for preparing para-xylene of alkylation of toluene and methanol has been carried out at home and abroad. The method uses cheap and easily available toluene and methanol as raw materials; the selectivity of PX in one reaction product is high, and expensive adsorption separation technology can be avoided in its production process. High purity para-xylene can be obtained by simple crystallization separation, and the content of benzene in the product is low. Metallic or/and non-metal modified HZSM-5 molecular sieve catalysts are mainly used. U.S. Pat. No. 4,250,345 uses phosphorus and magnesium two-element modified ZSM-5 molecular sieve catalyst with an optimum selectivity to para-xylene of ~98% at 450° C. Chinese patent CN101485994A reports a ZSM-5 catalyst modified by Pt, Si, Mg, P and mixed rare earth elements. The conversion rate of toluene is >20% and the selectivity of PX is >98%, when the molar ratio of toluene/methanol is 2/1 and the reaction temperature is 460° C. Chinese patent CN102716763A discloses a HZSM-5 molecular sieve catalyst modified by P, Ni element and $SiO_2$ deposition. The catalyst is used for alkylation reaction of toluene and methanol in a fixed bed reactor, and the conversion of toluene is ~31% and the selectivity of PX is ~91%.

The above reports indicate that, on the HZSM-5 molecular sieve catalyst, the reaction of preparing light olefins from methanol conversion can be achieved, and the reaction of preparing para-xylene by alkylation of methanol and toluene can also be achieved. However, due to the difference in the two reaction processes, there are also large differences in the physicochemical properties of the catalyst thereof. Therefore, a suitable modification method can be used to prepare a catalyst which can simultaneously satisfy the requirements of two reactions of: methanol conversion to prepare light olefins; and methanol and toluene alkylation to prepare para-xylene, so that the same catalyst can be used to simultaneously produce light olefins (ethylene, propylene) and para-xylene. Chinese patent CN101417236A discloses a fluidized bed catalyst for the alkylation of toluene and methanol to prepare para-xylene and light olefins, using the HZSM-5 molecular sieve catalyst modified by alkaline earth metal, non-metal, rare earth metal and siloxane-based compound. The selectivity of PX in the xylene product reaches 99%, the selectivity of ethylene and propylene in $C_1$-$C_5$ non-condensable gas is more than 90%, but the conversion of toluene is only ~20% and the conversion rate of methanol is not mentioned. In addition, the preparation process of this catalyst is complicated and requires multiple modifications and calcination processes.

Therefore, the development of a simple and easy-to-operate on-line preparation method of a catalyst for preparing para-xylene or light olefins and co-producing para-xylene is of great significance and significant practical applicability.

SUMMARY OF THE INVENTION

According to one aspect of the present application, this is provided an in-situ preparation method of a catalyst which is a catalyst for preparing para-xylene, toluene and/or light olefins from a raw material containing methanol and/or dimethyl ether, which is simple in process and easy-to-operate. By directly preparing the catalyst in the reaction system, the entire chemical production process is simplified, the catalyst preparation and transfer steps are saved, and the operation is easy. In the existing chemical industry, the traditional production mode of preparing the finished catalyst in the catalyst production unit and then transporting it to the chemical production unit to fill the catalyst and then start the production is broken, and the technical bias in the large-scale industrial production in the heterogeneous catalytic field is overcome.

The in-situ preparation method of a catalyst, wherein a Modifier is contacted with a molecular sieve in a reactor to in-situ prepare the catalyst for producing para-xylene, toluene and/or light olefins from a raw material containing methanol and/or dimethyl ether; and the reactor is a reactor for preparing para-xylene, toluene and/or light olefins from a raw material containing methanol and/or dimethyl ether.

Preferably, the Modifier comprises at least one of

Modifier I: a phosphorus reagent and a silylation reagent;

Modifier II: a silylation reagent;

Modifier III: a silylation reagent and water vapor;

Modifier IV: a phosphorus reagent, a silylation reagent and water vapor.

Preferably, the catalyst is a catalyst for at least one of the following reactions:

Reaction I: methanol and/or dimethyl ether, toluene to prepare light olefins and co-produce para-xylene;

Reaction II: methanol and/or dimethyl ether with benzene to prepare at least one of toluene, para-xylene and light olefins.

Preferably, the reactor is a reactor in which at least one of Reaction I or Reaction II Occurs.

As a preferred embodiment, Reaction I is to prepare para-xylene from methanol and/or dimethyl ether and benzene.

As a further preferred embodiment, Reaction I is to prepare para-xylene from methanol and toluene.

As an embodiment, Reaction II is to prepare toluene from methanol and/or dimethyl ether and benzene and co-produce para-xylene and light olefins.

As a preferred embodiment, Reaction II is to prepare toluene from methanol and/or dimethyl ether and benzene and co-produce para-xylene.

As a preferred embodiment, Reaction II is to prepare para-xylene from methanol and/or dimethyl ether and benzene and co-produce light olefins.

As a further preferred embodiment, Reaction II is to prepare para-xylene from methanol and/or dimethyl ether and benzene.

As a still further preferred embodiment, Reaction II is to prepare para-xylene from methanol and benzene.

In one embodiment, the phosphorus reagent is at least one selected from of the organophosphine compounds. Preferably, the phosphorus reagent is at least one selected from the compounds having the following formula (I):

(I)

$R_1$, $R_2$ and $R_3$ are independently selected from $C_{1-10}$ alkyl and $C_{1-10}$ alkoxy.

Further preferably, $R_1$, $R_2$ and $R_3$ in the formula (I) are independently selected from $C_{1-5}$ alkyl and $C_{1-5}$ alkoxy.

Preferably, at least one of $R_1$, $R_2$ and $R_3$ in the formula (I) is selected from $C_{1-10}$ alkoxy. Further preferably, at least one of $R_1$, $R_2$ and $R_3$ in the formula (I) is selected from $C_{1-5}$ alkoxy. Still more preferably, $R_1$, $R_2$ and $R_3$ in the formula (I) are the same alkoxy.

As one embodiment, the phosphorus reagent is at least one selected from trimethoxyphosphine, triethoxyphosphine, tripropoxyphosphine, tributoxyphosphine and methyldiethoxyphosphine.

As one embodiment, the silylation reagent is at least one selected from of organosilicon compounds. Preferably, the silylation reagent is at least one selected from the compounds having the following formula (II):

(II)

$R_4$, $R_5$, $R_6$ and $R_7$ are independently selected from $C_{1-10}$ alkyl and $C_{1-10}$ alkoxy.

Further preferably, $R_4$, $R_5$, $R_6$ and $R_7$ in the formula (II) are independently selected from $C_{1-5}$ alkyl and $C_{1-5}$ alkoxy.

Preferably, at least one of $R_4$, $R_5$, $R_6$ and $R_7$ in the formula (II) is selected from $C_{1-10}$ alkoxy. Further preferably, at least one of $R_4$, $R_5$, $R_6$ and $R_7$ in the formula (II) is selected from $C_{1-5}$ alkoxy. Still more preferably, $R_4$, $R_5$, $R_6$ and $R_7$ in the formula (II) are the same alkoxy.

As one embodiment, the phosphorus reagent is at least one selected from trimethoxyphosphine, triethoxyphosphine, tripropoxyphosphine, tributoxyphosphine and methyldiethoxyphosphine.

Preferably, the reactor is at least one selected from of a fixed bed reactor, a fluidized bed reactor and a moving bed reactor.

Preferably, the molecular sieve is a formed molecular sieve formed according to type of reactors;

the formed molecular sieve is composed of a molecular sieve; or the formed molecular sieve contains a molecular sieve and a binder.

As an alternative embodiment, the formed molecular sieve is prepared using one method selected from crushing a tablet obtained by tablet compressing of the molecular sieve; cutting a strip obtained by band extrusion of a mixture of the molecular sieve and the binder, and spray drying of a mixture of the molecular sieve and the binder.

Preferably, the molecule sieve is at least one selected from of the molecular sieves having MFI skeleton structure and the molecular sieves having MEL skeleton structure.

Further preferably, the molecular sieve is an HZSM-5 molecular sieve and/or HZSM-11 molecular sieve.

Preferably, the ratio (atomic ratio) of silicon to aluminum in the molecular sieve is Si/Al=5 to 35.

Preferably, the in-situ preparation method of the catalyst comprises at least the following steps:

(1) loading the formed molecular sieve in the reactor;

(2) feeding a feedstock containing a Modifier to the reactor;

(3) stopping feeding the feedstock containing the Modifier into the reactor, raising the temperature of the reactor to above 400° C. and introducing air to calcinate, to obtain the catalyst.

Preferably, the feedstock A in the step (2) comprises at least one of the raw materials and a Modifier.

Preferably, the feedstock A in the step (2) comprises toluene and/or benzene.

Preferably, the step (2) is to feed the feedstock A containing the Modifier I into the reactor; the Modifier I comprises a phosphorus reagent and a silylation reagent.

Further preferably, the feedstock A in the step (2) comprises the Modifier I and toluene.

Preferably, the step (2) is to feed the feedstock A containing a phosphorus reagent and a silylation reagent into the reactor at a temperature of 130° C. to 500° C.

Preferably, the feedstock A contains the phosphorus reagent, the silylation reagent and toluene.

Further preferably, the mass ratio of the phosphorus reagent to the silylation reagent in the feedstock A in the step (2) is:

silylation reagent: phosphorus reagent=1:2 to 5:1.

In the feedstock A, in addition to the phosphorus reagent, the silylation reagent and toluene, it is not excluded to contain other reagents which can improve the modification efficiency of the phosphorus reagent and the silylation reagent on the molecular sieve without affecting the reaction performance of the catalyst. Preferably, the amount of the phosphorus reagent in the feedstock A of the step (2) is 1 wt % to 10 wt % of the total weight of the feedstock A, the amount of the silylation reagent is 1 wt % to 40 wt % of the total weight of the feedstock A, and the amount of the toluene is 50 wt % to 98 wt % of the total weight of the feedstock A. Further preferably, the amount of the phosphorus reagent in the feedstock A of the step (2) is 2 wt % to 10 wt % of the total weight of the feedstock A, the amount of the silylation reagent is 8 wt % to 40 wt % of the total weight of the feedstock A, and the amount of the toluene is 50 wt % to 90 wt % of the total weight of the feedstock A.

One skilled in the art can adjust the space velocity and time of the feedstock A into the reactor in the step (2) according to the specific requirements in actual production.

Preferably, the total weight space velocity of the feedstock A fed into the reactor in the step (2) is in a range from 0.5 $h^{-1}$ to 2 $h^{-1}$.

Preferably, the time for feeding the feedstock A into the reactor in the step (2) is in a range from 30 min to 225 min.

Preferably, in step (3), the feedstock A is stopped from flowing into the reactor, and after being purged by the inert gas, the temperature is further raised to calcinate. Further preferably, the inert gas is at least one selected from nitrogen, helium and argon.

Preferably, the calcination temperature in the step (3) is in a range from 500° C. to 700° C., and the calcination time is in a period ranging from 1 hour to 6 hours.

Preferably, the step (2) is to feed the feedstock B containing the Modifier II into the reactor; the Modifier II comprises a silylation reagent.

Further preferably, the feedstock B in the step (2) comprises at least one of methanol, toluene, dimethyl ether; and the Modifier II.

Preferably, the step (2) is to feed the feedstock containing the Modifier III into the reactor; the modifier III comprises a silylation reagent and water vapor.

Preferably, the in-situ preparation method of the catalyst comprises at least the following steps:

(1) loading the formed molecular sieve in the reactor;

(2) feeding the feedstock D containing a silylation reagent into the reactor;

(3) stopping feeding feedstock D into the reactor, raising temperature of the reactor to above 500° C. and introducing air to calcinate;

(4) after purging with an inactive gas, when the temperature of the reactor is raised to above 550° C., subjecting the feedstock E containing water vapor for steam treatment, to obtain the catalyst.

Further preferably, the feedstock D in the step (2) comprises the silylation reagent and benzene.

Further preferably, the weight space velocity of the feedstock D in the step (2) is in a range from 0.1 $h^{-1}$ to 1 $h^{-1}$, and the time for feeding the feedstock D is in a range from 0.1 to 5 hours.

Further preferably, the weight space velocity of the feedstock D in the step (2) is 0.2 $h^{-1}$ to 0.4 $h^{-1}$, and the time for feeding the feedstock D is in a range of 0.5 to 2 hours.

Further preferably, the feedstock E in the step (4) comprises water vapor and benzene.

Preferably, the in-situ preparation method of the catalyst comprises at least the following steps:

(1) loading the formed molecular sieve in the reactor;

(2) feeding the feedstock F containing a phosphorus reagent and a silylation reagent into the reactor;

(3) stopping feeding the feedstock F into the reactor, raising the temperature of the reactor to above 500° C. and introducing air to calcinate;

(4) after purging with an inactive gas, when the temperature of the reactor is raised to above 550° C., subjecting the feedstock G containing water vapor for steam treatment, to obtain the catalyst.

Further preferably, the feedstock F in the step (2) comprises the phosphorus reagent, the silylation reagent and benzene.

Further preferably, the mass ratio of the silylation reagent to the phosphorus reagent in the feedstock F in the step (2) is:

silylation reagent: phosphorus reagent=1:2 to 5:1.

Further preferably, the calcination temperature in the step (3) is in a range from 500° C. to 700° C., and the calcination time is in a period ranging from 1 hour to 6 hours.

Further preferably, the inactive gas in the step (4) is at least one selected from nitrogen, helium and argon.

Further preferably, the temperature of the steam treatment in the step (4) is in a range from 550° C. to 800° C., and the treatment time is in a range from 1 to 10 hours.

Further preferably, the feedstock G in the step (4) comprises water vapor and benzene.

Preferably, the weight space velocity of the water vapor in the feedstock G in the step (4) is 0.5 $h^{-1}$ to 5 $h^{-1}$. Further preferably, the weight space velocity of the water vapor in the feedstock G in the step (4) is 1 $h^{1}$ to 3 $h^{-1}$.

The feedstock G containing water vapor may be 100% water vapor, or may be an inert gas and/or other agent which can improve (adjust) the steam reforming efficiency without affecting the catalyst reaction performance.

Preferably, the temperature of the steam treatment in the step (4) is in a range from 550° C. to 800° C., and the treatment time is in a range from 1 to 10 hours.

Preferably, the amount of the phosphorus reagent in the feedstock A of the step (2) is 1 wt % to 10 wt % of the total weight of the feedstock A, the amount of the silylation reagent is 1 wt % to 40 wt % of the total weight of the feedstock A, and the amount of the toluene is 50 wt % to 98 wt % of the total weight of the feedstock A.

Preferably, the amount of the phosphorus reagent in the feedstock F of the step (2) is 1 wt % to 10 wt % of the total weight of the feedstock F, the amount of the silylation reagent is 1 wt % to 40 wt % of the total weight of the feedstock F, and the amount of the benzene is 50 wt % to 98 wt % of the total weight of the feedstock F.

Preferably, the calcination temperature in the step (3) is in a range from 500° C. to 700° C., and the calcination time is in a period ranging from 1 hour to 6 hours.

Preferably, the step (2) is to feed the feedstock containing the Modifier into the reactor at temperature range from 130° C. to 500° C.

Preferably, the step (2) is to feed the feedstock containing the Modifier into the reactor at 200° C. to 400° C.

According to still another aspect of the present application, there is provided a process for preparing light olefins from methanol and/or dimethyl ether and toluene and co-producing para-xylene (Reaction I), wherein a raw material comprising methanol and/or dimethyl ether and toluene is contacted with the catalyst obtained according to any of the above in-situ preparation method in a reactor to prepare light olefins and co-produce para-xylene. That is, after the completion of the calcination of the modified catalyst, the reaction of preparing light olefins and co-producing paraxylene is started directly from the calcination temperature to the reaction temperature. Compared with the production method inherent in the chemical industry, the catalyst separation process after catalyst modification, the catalyst cooling process to room temperature after calcination, the catalyst transportation step, the catalyst charging step, and the high temperature preactivation after the catalyst is loaded into the reactor are saved. The production efficiency is greatly improved. The safety problems that may occur in the above saved steps are avoided. More importantly, the reaction is started by the reactor from the calcination temperature to the reaction temperature, the heat energy is fully utilized, and the energy consumption in production is greatly saved.

The process for carrying out Reaction I, wherein a raw material comprising methanol and/or dimethyl ether and toluene is contacted with the catalyst obtained by in-situ and on-line preparation method described in the above aspect in a reactor to prepare light olefins and co-produce para-xylene;

Reaction I is to prepare light olefins from methanol and/or dimethyl ether and toluene and co-produce para-xylene.

As a preferred embodiment, Reaction I is to prepare para-xylene from methanol and/or dimethyl ether and toluene.

As a preferred embodiment, Reaction I is to prepare para-xylene from methanol and toluene.

As a preferred embodiment, the silylation reagent and the water vapor are contacted with the molecular sieve in the reactor to in-situ prepare a catalyst of Reaction I; and the reactor is a reactor of Reaction I.

Preferably, the raw material is contacted with the catalyst at a reaction temperature ranging from 350° C. to 650° C.

Preferably, the raw material is contacted with the catalyst at a reaction temperature ranging from 400° C. to 500° C.

Preferably, in the raw material containing methanol and/or dimethyl ether and toluene, the ratio of methanol and/or dimethyl ether to toluene is as follows:

the number of carbon atoms of methanol and dimethyl ether: moles of toluene=0.5 to 10.

As an alternative embodiment, the reaction raw material contains methanol and toluene. Since methanol may be converted to dimethyl ether on the catalyst, that is, the interaction between methanol and dimethyl ether in the raw material is the same. Therefore, the reaction raw material fed actually contains methanol and toluene. Methanol, dimethyl ether and toluene are often present on the catalyst of the reactor. Although the following raw materials are exemplified by methanol and toluene, the case where dimethyl ether is contained in the raw material is not excluded. In the calculation, the number of moles of carbon atoms of dimethyl ether corresponds to the number of moles of methanol.

In the raw material containing methanol and toluene, the molar ratio of methanol to toluene is methanol:toluene=0.5 to 20:1. Preferably, in the raw material containing methanol and toluene, the molar ratio of methanol to toluene is methanol:toluene=1 to 15:1. Further preferably, in the raw material containing methanol and toluene, the molar ratio of methanol to toluene is methanol:toluene=5 to 15:1. In actual production, the ratio between light olefins and the para-xylene in the product can be adjusted by adjusting the ratio of methanol to toluene in the raw material according to specific production requirements. In general, when the methanol/toluene ratio in the raw material is increased, the content of olefin in the product is increased; when the methanol/toluene ratio in the raw material is reduced, the content of para-xylene in the product is increased.

Preferably, the total weight space velocity of the raw material containing methanol and toluene is in a range from 1 $h^{-1}$ to 3 $h^{-1}$.

Preferably, the material stream I is contacted with the catalyst in the reaction system to obtain the material stream II, and the $C_4$ olefin or the $C_{5+}$ chain hydrocarbon is separated from the material stream II and returned to a reaction system, light olefins and para-xylene separated from the material stream II are used as products;

the material stream I comprises methanol and/or dimethyl ether and toluene.

Further preferably, the reaction system comprises a first reaction zone and a second reaction zone, and the material stream I is contacted with the catalyst in the first reaction zone to obtain the material stream II-A, the $C_4$ olefin or the $C_{5+}$ chain hydrocarbon separated from the material stream II-A is fed into the second reaction zone and contacted with the catalyst to obtain the material stream II-B;

the $C_4$ olefin or the $C_{5+}$ chain hydrocarbon separated from the material stream II-B is returned to the second reaction zone;

light olefins and para-xylene separated from the material stream II-A and the material stream II-B are used as products.

Further preferably, the reaction system comprises a first reaction zone and a second reaction zone, and the material stream I is contacted with the catalyst in the first reaction zone to obtain a material stream II-A, the material stream II-A is fed to a separation system and the $C_4$ olefin, light olefins and para-xylene are separated;

the $C_4$ olefin separated in the separation system is fed into the second reaction zone to contact the catalyst to obtain a material stream II-B, the material stream II-B is fed into the separation system;

light olefins and para-xylene separated in the separation system are used as products.

Further preferably, the reaction system comprises a first reaction zone and a second reaction zone, and the material stream I is contacted with the catalyst in the first reaction zone to obtain the material stream II-A, the material stream II-A is fed to the separation system, and the $C_{5+}$ chain hydrocarbon, light olefins and para-xylene are output from the separation system;

the $C_{5+}$ chain hydrocarbon separated in the separation system is fed into the second reaction zone to contact the catalyst to obtain the material stream II-B, the material stream II-B is fed into the separation system; and light olefins and para-xylene output from the separation system are used as products.

Preferably, the reaction system comprises a first reaction zone and a second reaction zone, both the first reaction zone and the second reaction zone comprise a Catalyst A;

the Catalyst A is a HZSM-5 molecular sieve catalyst modified by a phosphorus reagent and a silylation reagent, the specific preparation steps of which are as follows:

(A1) the phosphorus reagent and the silylation reagent are fed into the first reaction zone with the HZSM-5 molecular sieve at the temperature ranging from 130° C. to 500° C.;

(A2) the temperature is raised to above 500° C., and calcined in an air atmosphere for 1-6 hours to obtain the Catalyst A.

Preferably, the reaction system comprises a first reaction zone containing a Catalyst A; and a second reaction zone containing a Catalyst B.

Further preferably, the Catalyst A is a HZSM-5 molecular sieve catalyst modified by a phosphorus reagent and a silylation reagent, the specific preparation steps of which are as follows:

(A1) a mixture of the phosphorus reagent, the silylation reagent and toluene is fed into the first reaction zone with the HZSM-5 molecular sieve at the temperature ranging from 130° C. to 500° C.;

(A2) the temperature is raised to above 500° C., and calcined in an air atmosphere for 1-6 hours to obtain the Catalyst A.

Further preferably, the Catalyst B is a HZSM-5 molecular sieve catalyst modified by a silylation reagent, the specific preparation steps of which are as follows:

(B1) a mixture of the silylation reagent and methanol is fed into the second reaction zone with the HZSM-5 molecular sieve at the temperature ranging from 120° C. to 250° C.;

(B2) the temperature is raised to above 500° C., and calcined in an air atmosphere for 1-6 hours to obtain the Catalyst B.

Preferably, the reaction system comprises one reactor or a plurality of reactors connected by series and/or parallel.

Further preferably, the reactor is at least one of a fixed bed reactor, a fluidized bed reactor or a moving bed reactor.

Preferably, the reaction system comprises a first reaction zone and a second reaction zone, and the first reaction zone and the second reaction zone are in the same reactor.

Preferably, the reaction system comprises a first reaction zone and a second reaction zone, the first reaction zone comprises one reactor or a plurality of reactors connected by series and/or parallel, and the second reaction zone comprises one reactor or a plurality of reactors connected by series and/or parallel.

Further preferably, the first reaction zone and the second reaction zone are connected by series or parallel.

In one embodiment of the present application, the first reaction zone undergoes a methanol conversion reaction and a toluene methanol alkylation reaction, and the second reaction zone undergoes a shape selective aromatization reaction.

Preferably, the total weight space velocity of the raw material is in a range from $0.1\ h^{-1}$ to $10\ h^{-1}$.

Preferably, the total weight space velocity of the raw material is in a range from $0.8\ h^{-1}$ to $3\ h^{-1}$.

Preferably, the molar content of toluene in the raw material is in a range from mol % to 50 mol %.

Preferably, the molar content of toluene in the raw material is in a range from mol % to 40 mol %.

Preferably, the phosphorus reagent and the silylation reagent are contacted with the molecular sieve in the reactor to in-situ prepare the catalyst for preparing light olefins and co-producing para-xylene; and the reactor is a reactor for preparing light olefins and co-producing para-xylene.

According to still another aspect of the present application, there is provided a process for preparing at least one of toluene, para-xylene, light olefins from methanol and/or dimethyl ether and benzene (Reaction II), wherein a raw material comprising methanol and/or dimethyl ether and benzene is contacted with the catalyst obtained according to any of the above in-situ preparation method in a reactor to prepare toluene, para-xylene and light olefins. That is, after the completion of the modification from Modifier I to Modifier IV, the reaction of preparing at least one of toluene, para-xylene and light olefins from methanol and/or dimethyl ether and benzene is started directly from the modification temperature to the reaction temperature. Compared with the production method inherent in the chemical industry, the catalyst separation process after catalyst modification, the catalyst cooling process to room temperature after calcination, the catalyst transportation step, the catalyst charging step, and the high temperature preactivation after the catalyst is loaded into the reactor are saved. The production efficiency is greatly improved. The safety problems that may occur in the above saved steps are avoided. More importantly, the reaction is started by the reactor from the calcination temperature to the reaction temperature, the heat energy is fully utilized, and the energy consumption in production is greatly saved.

The process for carrying out Reaction II, wherein a raw material comprising methanol and/or dimethyl ether and benzene is contacted with the catalyst obtained by in-situ and on-line preparation method described in the above aspect in a reactor to prepare toluene and co-produce para-xylene;

Reaction II is to prepare at least one of toluene, para-xylene and light olefins from methanol and/or dimethyl ether.

Preferably, the silylation reagent and the water vapor are contacted with the molecular sieve in the reactor to in-situ prepare a catalyst of Reaction II; and the reactor is a reactor of Reaction II.

After the completion of the water vapor modification, the reaction of preparing toluene and co-producing para-xylene by alkylation from methanol and/or dimethyl ether and benzene is started directly from the water vapor modification temperature to the reaction temperature. Compared with the production method inherent in the chemical industry, the catalyst separation process after catalyst modification, the catalyst cooling process to room temperature after calcination, the catalyst transportation step, the catalyst charging step, and the high temperature preactivation after the catalyst is loaded into the reactor are saved. The production efficiency is greatly improved. The safety problems that may occur in the above saved steps are avoided. More importantly, the reaction is started by the reactor from the calcination temperature to the reaction temperature, the heat energy is fully utilized, and the energy consumption in production is greatly saved.

The raw material in the present application contains benzene and methanol, in which methanol includes methanol and/or dimethyl ether in the form of feed. Since methanol may be converted to dimethyl ether on the catalyst, that is, the interaction between methanol and dimethyl ether in the raw material is the same. Therefore, the reaction raw material fed actually contains methanol and toluene. Methanol, dimethyl ether and toluene are often present on the catalyst of the reactor. Although the following raw materials are exemplified by methanol and toluene, the case where dimethyl ether is contained in the raw material is not excluded. In the calculation, the number of moles of carbon atoms of dimethyl ether corresponds to the number of moles of methanol.

In the present application, benzene and methanol is used to prepare para-xylene and light olefins, wherein the raw material contains benzene and methanol, and the case where methanol includes methanol and/or dimethyl ether. Unless otherwise specified, the methanol in the present application may be replaced by all or part of dimethyl ether and the amount of methanol may be calculated by converting dimethyl ether into methanol having the same number of carbon atoms.

Further preferably, the reactor is at least one selected from of a fixed bed reactor, a fluidized bed reactor and a moving bed reactor.

Preferably, the reaction temperature of Reaction II is in a range from 350° C. to 600° C.

Preferably, the reaction temperature of Reaction II is in a range from 400° C. to 500° C.

In the raw material containing methanol and benzene, the molar ratio of methanol to benzene is methanol:benzene=0.5 to 10:1. Preferably, in the raw material containing methanol and benzene, the molar ratio of methanol to benzene is methanol:benzene=1 to 5:1. Further preferably, in the raw material containing methanol and benzene, the molar ratio of methanol to benzene is methanol:benzene=1 to 2:1. In actual production, the ratio between light olefins and the toluene, para-xylene in the product can be adjusted by adjusting the ratio of methanol to benzene in the raw material according to specific production requirements. In general, when the methanol/benzene ratio in the raw material is increased, the content of olefin in the product is increased; when the methanol/benzene ratio in the raw material is reduced, the content of toluene and para-xylene in the product is increased.

Preferably, in the raw material containing methanol and benzene, the molar ratio of methanol to benzene is methanol:benzene=(0.5 to 2):1. Further preferably, in the raw material containing methanol and benzene, the molar ratio of methanol to benzene is methanol:benzene=(1 to 1.5):1.

Preferably, the total weight space velocity of the raw materials containing methanol and benzene is 1 $h^{-1}$ to 4 $h^{-1}$.

Preferably, the in-situ preparation method of the catalyst of Reaction II comprises at least the following steps:

(1) loading the formed molecular sieve in the reactor;

(2) feeding the material D containing a silylation reagent and benzene into the reactor;

(3) stopping feeding the feedstock D into the reactor, raising the temperature of the reactor to above 500° C. and introducing air to calcinate;

(4) after purging with an inactive gas, when the temperature of the reactor is raised to above 550° C., subjecting the feedstock E containing water vapor for steam treatment, to obtain the catalyst of Reaction II.

Preferably, the in-situ preparation method of the catalyst of Reaction II comprises at least the following steps:

(1) loading the formed molecular sieve in the reactor;

(2) feeding the feedstock F containing a phosphorus reagent, a silylation reagent and benzene into the reactor;

(3) stopping feeding the feedstock F into the reactor, raising the temperature of the reactor to above 500° C. and introducing air to calcinate;

(4) after purging with an inactive gas, when the temperature of the reactor is raised to above 550° C., subjecting the feedstock G containing water vapor for steam treatment, to obtain the catalyst of Reaction II.

In the present application, the reaction raw material contains methanol and the case where methanol includes methanol and/or dimethyl ether. Unless otherwise specified, the methanol in the present application may be replaced by all or part of dimethyl ether and the amount of methanol may be calculated by converting dimethyl ether into methanol having the same number of carbon atoms.

In the present application, the above-mentioned $C_1$~$C_{10}$, $C_1$~$C_5$ and the like refer to the number of carbon atoms contained in the group.

In the present application, the "alkyl" is a group formed by the loss of any one of the hydrogen atoms in the molecule of the alkane compound. The alkane compound includes a linear alkane, a branched alkane, a cycloalkane, a branched cycloalkane.

In the present application, the "alkoxy" is a group formed by the loss of a hydrogen atom on a hydroxyl group from an alkyl alcohol compound.

In the present application, the "light olefins" means ethylene and propylene.

In the present application, the "methanol and/or dimethyl ether and toluene" includes three cases: methanol and toluene; or dimethyl ether and toluene; or methanol, dimethyl ether and toluene.

In the present application, the "methanol and/or dimethyl ether and benzene" includes three cases: methanol and benzene; or dimethyl ether and benzene; or methanol, dimethyl ether and benzene.

Unless otherwise specified, the methanol in the present application may be replaced by all or part of dimethyl ether and the amount of methanol may be calculated by converting dimethyl ether into methanol having the same number of carbon atoms.

The benefits brought out by the present application include, but are not limited to:

(1) The in-situ preparation method of the catalyst for preparing at least one of toluene, para-xylene and light olefins, provided by the present application, breaks the traditional production mode of preparing the finished catalyst in the catalyst production unit and then transporting it to the chemical production unit to fill the catalyst and then start the production, in the existing chemical industry, and overcomes the technical bias in large-scale industrial production in the field of heterogeneous catalysis.

(2) The in-situ preparation method of the catalyst for preparing at least one of toluene, para-xylene and light olefins, provided by the present application, simplifies the entire chemical production process, saves catalyst preparation and transfer steps, and is easy to operate.

(3) The method for preparing at least one of toluene, para-xylene and light olefins, provided by the present application, compared with the production method inherent in the chemical industry, saves the catalyst separation process after catalyst modification, the catalyst cooling process to room temperature after calcination, the catalyst transportation step, the catalyst charging step, and the high temperature pre-activation after the catalyst is loaded into the reactor. The production efficiency is greatly improved. The safety problems that may occur in the above saved steps are avoided. More importantly, the reaction is started by the reactor from the calcination temperature to the reaction temperature, the heat energy is fully utilized, and the energy consumption in production is greatly saved.

(4) The method for preparing at least one of toluene, para-xylene and light olefins, provided by the present application, from catalyst preparation to reaction, is completed in situ in a system, and is beneficial to the recovery and recycling of waste in the preparation process of the catalyst in large-scale chemical production, and is environmentally friendly.

(5) The method for preparing at least one of toluene, para-xylene and light olefins from methanol and/or dimethyl ether and toluene, provided by the present application, the conversion rate of methanol is 100%, and the selectivity of para-xylene in xylene is as high as 99.6 wt % or more.

(6) The method for preparing at least one of toluene, para-xylene and light olefins from methanol and/or dimethyl ether and benzene, provided by the present application, the conversion of methanol is 100%, the selectivity of (toluene+para-xylene) in the aromatic product is >85 wt %, the selectivity of para-xylene in the xylene product is >99.6 wt %, and the selectivity of para-xylene in the $C_8$ aromatics is >90 wt %.

DETAILED DESCRIPTION OF THE EMBODIMENT

Figure 1:
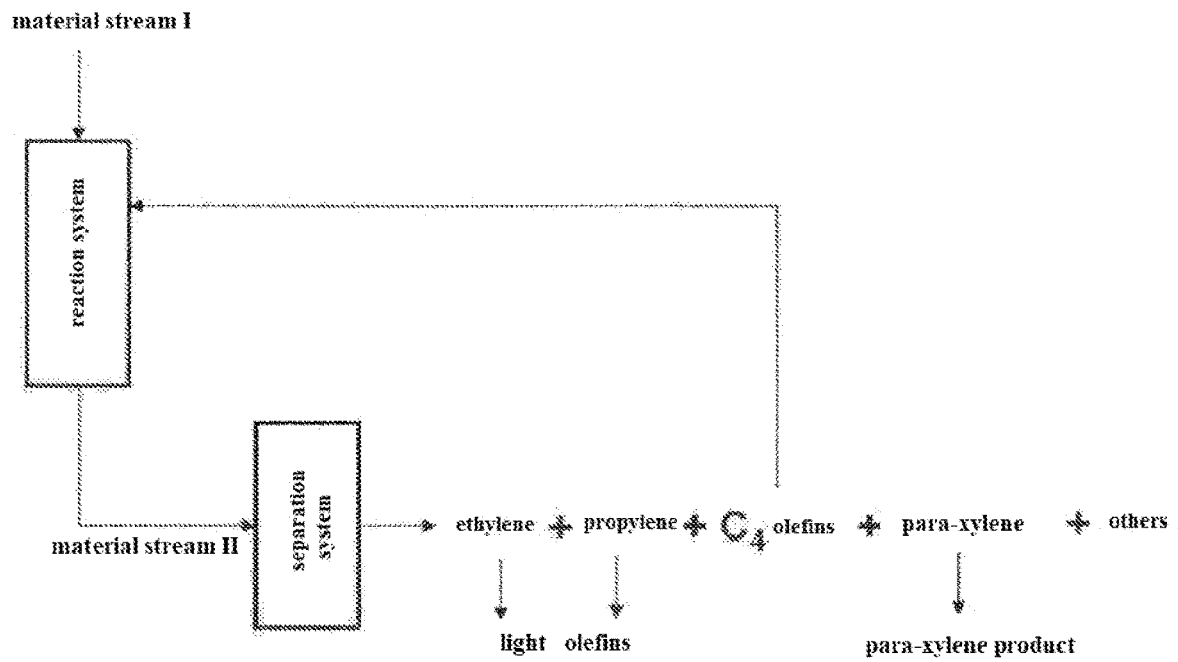
FIG. 1 is a process flow diagram of an embodiment of the application of the present application.

The present application will be described in detail below with reference to the embodiments, but the application is not limited to these embodiments.

Unless otherwise specified, the raw materials and reagents used in this application are all commercially available and used without treatment. The equipment used is based on the manufacturer's recommended scheme and parameters.

In the examples, the wear index of the catalyst was measured on an MS-C type wear indexer of Shenyang Hexing Machinery & Electronics Co., Ltd.

In the examples, the fixed bed reactor has an inner diameter of 1.5 cm; the fixed fluidized bed reactor has an inner diameter of 3 cm; and the circulating fluidized bed reactor has an inner diameter of 12 cm.

Example 1: Preparation of HZSM-5 Formed Molecular Sieve Sample For Fixed Bed 100 g of HZSM-5 zeolite molecular sieve raw powder (Nankai University Catalyst Factory, Si/Al=30) was calcined in an air atmosphere at 550° C. for 4 hours, then tableted and crushed, and sieved to obtain formed molecular sieve particles with particle size of 40 to 60 mesh, recorded as FXHZSM-5-A.

100 g of HZSM-5 zeolite molecular sieve raw powder (Nankai University Catalyst Factory, Si/Al=5) was calcined in an air atmosphere at 550° C. for 4 hours, then tableted and crushed, and sieved to obtain formed molecular sieve particles with particle size of 40 to 60 mesh, recorded as FXHZSM-5-B.

100 g of HZSM-5 zeolite molecular sieve raw powder (Nankai University Catalyst Factory, Si/Al=10) was calcined in an air atmosphere at 550° C. for 4 hours, then tableted and crushed, and sieved to obtain formed molecular sieve particles with particle size of 40 to 60 mesh, recorded as FXHZSM-5-C.

Example 2: Preparation of HZSM-11 Formed Molecular Sieve Sample for Fixed Bed 100 g of HZSM-11 zeolite molecular sieve raw powder (Nankai University Catalyst Factory, Si/Al=35) was calcined in an air atmosphere at 550° C. for 4 hours, then tableted and crushed, and sieved to obtain formed molecular sieve particles with particle size of 40 to 60 mesh, recorded as FXHZSM-11-A.

100 g of HZSM-11 zeolite molecular sieve raw powder (Nankai University Catalyst Factory, Si/Al=12) was calcined in an air atmosphere at 550° C. for 4 hours, then tableted and crushed, and sieved to obtain formed molecular sieve particles with particle size of 40 to 60 mesh, recorded as FXHZSM-11-B.

Example 3: Preparation of HZSM-5 Formed Molecular Sieve Sample for Fluidized Bed 100 g of HZSM-5 zeolite molecular sieve raw powder (Nankai University Catalyst Factory, Si/Al=30) was spray-dried with aluminum- or silicon-containing amorphous binder. The specific steps were as follows:

HZSM-5 zeolite molecular sieve raw powder, pseudo-boehmite, silica sol, xanthan gum (bio-gel) and water were uniformly mixed, and the slurry was obtained by beating, grinding and defoaming; the parts by weight of each component in the slurry was:

| | |
|---|---|
| HZSM-5 | 40 parts by weight |
| $Al_2O_3$ | 20 parts by weight |
| $SiO_2$ | 40 parts by weight |
| $H_2O$ | 240 parts by weight |
| Xanthan gum | 1 part by weight |

The obtained slurry was spray-dried to obtain a sample of microsphere particles having a particle size distribution of 20 to 100 jam; and the sample of the microsphere particles was calcined at 550° C. for 3 hours in a muffle furnace to obtain a HZSM-5 formed molecular sieve having a wear index of 1.2, recorded as FLHZSM-5-A.

Example 4: Preparation of HZSM-5 Formed Molecular Sieve Sample for Fluidized Bed The specific preparation conditions and steps were the same as those in Example 3, except that the raw material HZSM-5 zeolite molecular sieve raw powder is used in an amount of 10 kg, and the obtained microsphere particle sample has a particle size distribution of 20 to 120 m and a wear index of 1.2, recorded as FLHZSM-5-B.

The specific preparation conditions and steps were the same as those in Example 3, except that the raw material HZSM-5 zeolite molecular sieve raw powder has a silicon-aluminum ratio Si/Al=10, and the obtained microsphere particle sample has a particle size distribution of 20 to 100 m and a wear index of 1.2, recorded as FLHZSM-5-C.

Example 5: Preparation and Reaction Evaluation of Catalyst FXCAT-1 for Fixed Bed The reaction performance of on-line preparing fixed bed catalyst for preparing light olefins from methanol and toluene and co-producing para-xylene in a fixed bed microreactor was evaluated.

The conditions for preparing the catalyst on-line were as follows: 5 g of (40 to 60 mesh) formed molecular sieve sample FXHZSM-5-A was loaded into the fixed bed reactor, first treated with 50 mL/min of nitrogen at 550° C. for 1 hour, and then cooled to 200° C. under a nitrogen atmosphere. A mixture of trimethoxyphosphine, tetraethyl silicate and toluene was fed with a micro feed pump, trimethoxyphosphine:tetraethyl silicate:toluene (weight ratio)=5:20:75. The total weight space velocity of trimethoxyphosphine, tetraethyl silicate and toluene was 1 $h^{-1}$, at atmospheric pressure. After feeding for 90 minutes, the feed was stopped, and after nitrogen purge, the temperature was raised to 550° C., and calcined in an air atmosphere for 4 hours to obtain a fixed bed catalyst for preparing light olefins and co-producing para-xylene from methanol and toluene, which was named FXCAT-1. Then, the temperature was lowered to a reaction temperature of 450° C. under a nitrogen atmosphere, and the reaction of preparing light olefins and co-producing para-xylene from methanol and toluene was carried out. The reaction conditions were as follows: the raw materials were fed with a micro feed pump. Methanol: toluene (molar ratio) in the raw material=10:1, the total weight space velocity of methanol and toluene was 2 h$^{-1}$, at atmospheric pressure. The reaction product was analyzed by on-line Agilent 7890 gas chromatography, and the sample was analyzed at 60 min. The reaction results were shown in Table 1.

TABLE 1

| Catalyst | FXCAT-1 |
| --- | --- |
| Reaction Temperature (° C.) | 450 |
| Conversion Rate of Methanol (%) | 100 |
| Conversion Rate of Toluene (%) | 36.09 |
| Selectivity of Para-xylene in Xylene Isomers (wt %) | 99.64 |
| Product Distribution (wt %) | |
| Chain Hydrocarbon | 77.74 |
| Benzene | 0.06 |
| Ethylbenzene | 0.25 |
| Para-xylene | 19.26 |
| M-xylene | 0.04 |
| O-xylene | 0.03 |
| C$_{9+}$ Aromatic Hydrocarbon | 2.61 |
| Distribution of chain hydrocarbon products (wt %) | |
| CH$_4$ | 1.26 |
| C$_2$H$_4$ | 39.84 |
| C$_2$H$_6$ | 0.1 |
| C$_3$H$_6$ | 35.32 |
| C$_3$H$_8$ | 0.89 |
| C$_4$ | 11.99 |
| C$_5$ | 5.06 |
| C$_{6+}$ | 5.53 |
| C$_2$H$_4$ + C$_3$H$_6$ | 75.16 |

Example 6: Preparation and Reaction Evaluation of Catalyst FXCAT-2 for Fixed Bed The reaction performance of on-line preparing fixed bed catalyst for preparing light olefins from methanol and toluene and co-producing para-xylene in a fixed bed microreactor was evaluated.

The conditions for preparing the catalyst on-line were as follows: 5 g of (40 to 60 mesh) formed molecular sieve sample FXHZSM-5-A was loaded into the fixed bed microreactor, first treated with 50 mL/min of nitrogen at 550° C. for 1 hour, and then cooled to 200° C. under a nitrogen atmosphere. A mixture of trimethoxyphosphine, tetraethyl silicate and toluene was fed with a micro feed pump, trimethoxyphosphine:tetraethyl silicate:toluene (weight ratio)=10:40:50. The total weight space velocity of trimethoxyphosphine, tetraethyl silicate and toluene was 1 h$^{-1}$, at atmospheric pressure. After feeding for 45 minutes, the feed was stopped, and after nitrogen purge, the temperature was raised to 550° C., and calcined in an air atmosphere for 4 hours to obtain a fixed bed catalyst for preparing light olefins and co-producing para-xylene from methanol and toluene, which was named FXCAT-2. Then, the temperature was lowered to a reaction temperature of 450° C. under a nitrogen atmosphere, and the reaction of preparing light olefins and co-producing para-xylene from methanol and toluene was carried out. The reaction conditions were as follows: the raw materials were fed with a micro feed pump. Methanol: toluene (molar ratio) in the raw material=10:1, the total weight space velocity of methanol and toluene was 2 h$^{-1}$, at atmospheric pressure. The reaction product was analyzed by on-line Agilent 7890 gas chromatography, and the sample was analyzed at 60 min. The reaction results were shown in Table 2.

TABLE 2

| Catalyst | FXCAT-2 |
| --- | --- |
| Reaction Temperature (° C.) | 450 |
| Conversion Rate of Methanol (%) | 100 |
| Conversion Rate of Toluene (%) | 36.68 |
| Selectivity of Para-xylene in Xylene Isomers (wt %) | 99.64 |
| Product Distribution (wt %) | |
| Chain Hydrocarbon | 77.59 |
| Benzene | 0.08 |
| Ethylbenzene | 0.29 |
| Para-xylene | 19.18 |
| M-xylene | 0.04 |
| O-xylene | 0.03 |
| C$_{9+}$ Aromatic Hydrocarbon | 2.79 |
| Distribution of chain hydrocarbon products (wt %) | |
| CH$_4$ | 1.23 |
| C$_2$H$_4$ | 39.76 |
| C$_2$H$_6$ | 0.13 |
| C$_3$H$_6$ | 35.25 |
| C$_3$H$_8$ | 0.96 |
| C$_4$ | 12.06 |
| C$_5$ | 5.11 |
| C$_{6+}$ | 5.5 |
| C$_2$H$_4$ + C$_3$H$_6$ | 75.01 |

Example 7: Preparation and Reaction Evaluation of Catalyst FXCAT-3 for Fixed Bed The reaction performance of on-line preparing fixed bed catalyst for preparing light olefins from methanol and toluene and co-producing para-xylene in a fixed bed microreactor was evaluated.

The conditions for preparing the catalyst on-line were as follows: 5 g of (40 to 60 mesh) formed molecular sieve sample FXHZSM-5-A was loaded into the fixed bed microreactor, first treated with 50 mL/min of nitrogen at 550° C. for 1 hour, and then cooled to 200° C. under a nitrogen atmosphere. A mixture of trimethoxyphosphine, tetraethyl silicate and toluene was fed with a micro feed pump, trimethoxyphosphine:tetraethyl silicate:toluene (weight ratio)=2:8:90. The total weight space velocity of trimethoxyphosphine, tetraethyl silicate and toluene was 1 h$^{-1}$, at atmospheric pressure. After feeding for 225 minutes, the feed was stopped, and after nitrogen purge, the temperature was raised to 550° C., and calcined in an air atmosphere for 4 hours to obtain a fixed bed catalyst for preparing light olefins and co-producing para-xylene from methanol and toluene, which was named FXCAT-3. Then, the temperature was lowered to a reaction temperature of 450° C. under a nitrogen atmosphere, and the reaction of preparing light olefins and co-producing para-xylene from methanol and toluene was carried out. The reaction conditions were as follows: the raw materials were fed with a micro feed pump. Methanol: toluene (molar ratio) in the raw material=10:1, the total weight space velocity of methanol and toluene was 2 h$^{-1}$, at atmospheric pressure. The reaction product was analyzed by on-line Agilent 7890 gas chromatography, and the sample was analyzed at 60 min. The reaction results were shown in Table 3.

TABLE 3

| Catalyst | FXCAT-3 |
|---|---|
| Reaction Temperature (° C.) | 450 |
| Conversion Rate of Methanol (%) | 100 |
| Conversion Rate of Toluene (%) | 35.59 |
| Selectivity of Para-xylene in Xylene Isomers (wt %) | 99.69 |
| Product Distribution (wt %) | |
| Chain Hydrocarbon | 77.9 |
| Benzene | 0.06 |
| Ethylbenzene | 0.21 |
| Para-xylene | 19.19 |
| M-xylene | 0.03 |
| O-xylene | 0.03 |
| $C_{9+}$ Aromatic Hydrocarbon | 2.58 |
| Distribution of chain hydrocarbon products (wt %) | |
| $CH_4$ | 1.31 |
| $C_2H_4$ | 39.91 |
| $C_2H_6$ | 0.09 |
| $C_3H_6$ | 35.46 |
| $C_3H_8$ | 0.83 |
| $C_4$ | 11.91 |
| $C_5$ | 5.01 |
| $C_{6+}$ | 5.48 |
| $C_2H_4 + C_3H_6$ | 75.37 |

Example 8: Preparation and Reaction Evaluation of Catalyst FXCAT-4 for Fixed Bed The reaction performance of on-line preparing fixed bed catalyst for preparing light olefins from methanol and toluene and co-producing para-xylene in a fixed bed microreactor was evaluated.

The conditions for preparing the catalyst on-line were as follows: 5 g of (40 to 60 mesh) formed molecular sieve sample FXHZSM-5-A was loaded into the fixed bed microreactor, first treated with 50 mL/min of nitrogen at 550° C. for 1 hour, and then cooled to 300° C. under a nitrogen atmosphere. A mixture of trimethoxyphosphine, tetraethyl silicate and toluene was fed with a micro feed pump, trimethoxyphosphine:tetraethyl silicate:toluene (weight ratio)=5:20:75. The total weight space velocity of trimethoxyphosphine, tetraethyl silicate and toluene was 1 $h^{-1}$, at atmospheric pressure. After feeding for 90 minutes, the feed was stopped, and after nitrogen purge, the temperature was raised to 550° C., and calcined in an air atmosphere for 4 hours to obtain a fixed bed catalyst for preparing light olefins and co-producing para-xylene from methanol and toluene, which was named FXCAT-4. Then, the temperature was lowered to a reaction temperature of 450° C. under a nitrogen atmosphere, and the reaction of preparing light olefins and co-producing para-xylene from methanol and toluene was carried out. The reaction conditions were as follows: the raw materials were fed with a micro feed pump. Methanol: toluene (molar ratio) in the raw material=10:1, the total weight space velocity of methanol and toluene was 2 $h^{-1}$, at atmospheric pressure. The reaction product was analyzed by on-line Agilent 7890 gas chromatography, and the sample was analyzed at 60 min. The reaction results were shown in Table 4.

TABLE 4

| Catalyst | FXCAT-4 |
|---|---|
| Reaction Temperature (° C.) | 450 |
| Conversion Rate of Methanol (%) | 100 |
| Conversion Rate of Toluene (%) | 35.20 |
| Selectivity of Para-xylene in Xylene Isomers (wt %) | 99.90 |
| Product Distribution (wt %) | |
| Chain Hydrocarbon | 77.58 |
| Benzene | 0.09 |
| Ethylbenzene | 0.35 |
| Para-xylene | 20.33 |
| M-xylene | 0.01 |
| O-xylene | 0.01 |
| $C_{9+}$ Aromatic Hydrocarbon | 1.63 |
| Distribution of chain hydrocarbon products (wt %) | |
| $CH_4$ | 1.11 |
| $C_2H_4$ | 41.57 |
| $C_2H_6$ | 0.1 |
| $C_3H_6$ | 36.98 |
| $C_3H_8$ | 1.18 |
| $C_4$ | 12.21 |
| $C_5$ | 3.43 |
| $C_{6+}$ | 3.42 |
| $C_2H_4 + C_3H_6$ | 78.55 |

Example 9: Preparation and Reaction Evaluation of Catalyst FXCAT-5 for Fixed Bed The reaction performance of on-line preparing fixed bed catalyst for preparing light olefins from methanol and toluene and co-producing para-xylene in a fixed bed microreactor was evaluated.

The conditions for preparing the catalyst on-line were as follows: 5 g of (40 to 60 mesh) formed molecular sieve sample FXHZSM-5-A was loaded into the fixed bed microreactor, first treated with 50 mL/min of nitrogen at 550° C. for 1 hour, and then cooled to 450° C. under a nitrogen atmosphere. A mixture of trimethoxyphosphine, tetraethyl silicate and toluene was fed with a micro feed pump, trimethoxyphosphine:tetraethyl silicate:toluene (weight ratio)=5:20:75. The total weight space velocity of trimethoxyphosphine, tetraethyl silicate and toluene was 1 $h^{-1}$, at atmospheric pressure. After feeding for 90 minutes, the feed was stopped, and after nitrogen purge, the temperature was raised to 550° C., and calcined in an air atmosphere for 4 hours to obtain a fixed bed catalyst for preparing light olefins and co-producing para-xylene from methanol and toluene, which was named FXCAT-5. Then, the temperature was lowered to a reaction temperature of 450° C. under a nitrogen atmosphere, and the reaction of preparing light olefins and co-producing para-xylene from methanol and toluene was carried out. The reaction conditions were as follows: the raw materials were fed with a micro feed pump. Methanol: toluene (molar ratio) in the raw material=10:1, the total weight space velocity of methanol and toluene was 2 $h^{-1}$, at atmospheric pressure. The reaction product was analyzed by on-line Agilent 7890 gas chromatography, and the sample was analyzed at 60 min. The reaction results were shown in Table 5.

TABLE 5

| Catalyst | FXCAT-5 |
|---|---|
| Reaction Temperature (° C.) | 450 |
| Conversion Rate of Methanol (%) | 100 |
| Conversion Rate of Toluene (%) | 35.80 |
| Selectivity of Para-xylene in Xylene Isomers (wt %) | 99.63 |
| Product Distribution (wt %) | |

TABLE 5-continued

| Catalyst | FXCAT-5 |
|---|---|
| Chain Hydrocarbon | 75.29 |
| Benzene | 0.07 |
| Ethylbenzene | 0.35 |
| Para-xylene | 21.32 |
| M-xylene | 0.05 |
| O-xylene | 0.03 |
| $C_{9+}$ Aromatic Hydrocarbon | 2.89 |
| Distribution of Chain Hydrocarbon Products (wt %) | |
| $CH_4$ | 1.08 |
| $C_2H_4$ | 40.96 |
| $C_2H_6$ | 0.11 |
| $C_3H_6$ | 36.49 |
| $C_3H_8$ | 1.41 |
| $C_4$ | 12.65 |
| $C_5$ | 3.76 |
| $C_{6+}$ | 3.54 |
| $C_2H_4 + C_3H_6$ | 77.45 |

Example 10: Preparation and Reaction Evaluation of Catalyst FXCAT-6 for Fixed Bed The reaction performance of on-line preparing fixed bed catalyst for preparing light olefins from methanol and toluene and co-producing para-xylene in a fixed bed microreactor was evaluated.

The conditions for preparing the catalyst on-line were as follows: 5 g of (40 to 60 mesh) formed molecular sieve sample FXHZSM-5-A was loaded into the fixed bed microreactor, first treated with 50 mL/min of nitrogen at 550° C. for 1 hour, and then cooled to 150° C. under a nitrogen atmosphere. A mixture of trimethoxyphosphine, tetraethyl silicate and toluene was fed with a micro feed pump, trimethoxyphosphine:tetraethyl silicate:toluene (weight ratio)=5:20:75. The total weight space velocity of trimethoxyphosphine, tetraethyl silicate and toluene was 1 $h^{-1}$, at atmospheric pressure. After feeding for 90 minutes, the feed was stopped, and after nitrogen purge, the temperature was raised to 550° C., and calcined in an air atmosphere for 4 hours to obtain a fixed bed catalyst for preparing light olefins and co-producing para-xylene from methanol and toluene, which was named FXCAT-6. Then, the temperature was lowered to a reaction temperature of 450° C. under a nitrogen atmosphere, and the reaction of preparing light olefins and co-producing para-xylene from methanol and toluene was carried out. The reaction conditions were as follows: the raw materials were fed with a micro feed pump. Methanol: toluene (molar ratio) in the raw material=10:1, the total weight space velocity of methanol and toluene was 2 $h^{-1}$, at atmospheric pressure. The reaction product was analyzed by on-line Agilent 7890 gas chromatography, and the sample was analyzed at 60 min. The reaction results were shown in Table 6.

TABLE 6

| Catalyst | FXCAT-6 |
|---|---|
| Reaction Temperature (° C.) | 450 |
| Conversion Rate of Methanol (%) | 100 |
| Conversion Rate of Toluene (%) | 34.79 |
| Selectivity of Para-xylene in Xylene Isomers (wt %) | 99.95 |
| Product Distribution (wt %) | |
| Chain Hydrocarbon | 78.37 |
| Benzene | 0.08 |
| Ethylbenzene | 0.21 |
| Para-xylene | 19.98 |
| M-xylene | 0 |
| O-xylene | 0.01 |
| $C_{9+}$ Aromatic Hydrocarbon | 1.35 |
| Distribution of Chain Hydrocarbon Products (wt %) | |
| $CH_4$ | 0.96 |
| $C_2H_4$ | 41.03 |
| $C_2H_6$ | 0.11 |
| $C_3H_6$ | 37.96 |
| $C_3H_8$ | 1.03 |
| $C_4$ | 11.01 |
| $C_5$ | 4.08 |
| $C_{6+}$ | 3.82 |
| $C_2H_4 + C_3H_6$ | 78.99 |

Example 11: Preparation and Reaction Evaluation of Catalyst FXCAT-7 for Fixed Bed The reaction performance of on-line preparing fixed bed catalyst for preparing light olefins from methanol and toluene and co-producing para-xylene in a fixed bed microreactor was evaluated.

The conditions for preparing the catalyst on-line were as follows: 5 g of (40 to 60 mesh) formed molecular sieve sample FXHZSM-11-A was loaded into the fixed bed microreactor, first treated with 50 mL/min of nitrogen at 550° C. for 1 hour, and then cooled to 300° C. under a nitrogen atmosphere. A mixture of trimethoxyphosphine, tetraethyl silicate and toluene was fed with a micro feed pump, trimethoxyphosphine:tetraethyl silicate:toluene (weight ratio)=5:20:75. The total weight space velocity of trimethoxyphosphine, tetraethyl silicate and toluene was 1 $h^{-1}$, at atmospheric pressure. After feeding for 90 minutes, the feed was stopped, and after nitrogen purge, the temperature was raised to 550° C., and calcined in an air atmosphere for 4 hours to obtain a fixed bed catalyst for preparing light olefins and co-producing para-xylene from methanol and toluene, which was named FXCAT-7. Then, the temperature was lowered to a reaction temperature of 450° C. under a nitrogen atmosphere, and the reaction of preparing light olefins and co-producing para-xylene from methanol and toluene was carried out. The reaction conditions were as follows: the raw materials were fed with a micro feed pump. Methanol: toluene (molar ratio) in the raw material=10:1, the total weight space velocity of methanol and toluene was 2 $h^{-1}$, at atmospheric pressure. The reaction product was analyzed by on-line Agilent 7890 gas chromatography, and the sample was analyzed at 60

TABLE 7

| Catalyst | FXCAT-7 |
|---|---|
| Reaction Temperature (° C.) | 450 |
| Conversion Rate of Methanol (%) | 100 |
| Conversion Rate of Toluene (%) | 33.58 |
| Selectivity of Para-xylene in Xylene Isomers (wt %) | 99.90 |
| Product Distribution (wt %) | |
| Chain Hydrocarbon | 77.79 |
| Benzene | 0.07 |
| Ethylbenzene | 0.28 |
| Para-xylene | 19.88 |
| M-xylene | 0.01 |
| O-xylene | 0.01 |
| $C_{9+}$ Aromatic Hydrocarbon | 1.96 |

TABLE 7-continued

| Catalyst | FXCAT-7 |
|---|---|
| Distribution of chain hydrocarbon products (wt %) | |
| $CH_4$ | 0.85 |
| $C_2H_4$ | 40.51 |
| $C_2H_6$ | 0.11 |
| $C_3H_6$ | 37.79 |
| $C_3H_8$ | 0.83 |
| $C_4$ | 10.57 |
| $C_5$ | 4.53 |
| $C_{6+}$ | 4.81 |
| $C_2H_4 + C_3H_6$ | 78.30 |

Example 12: Preparation and Reaction Evaluation of Catalyst FLCAT-1 for Fluidized Bed The reaction performance of on-line preparing fluidized bed catalyst for preparing para-xylene from methanol and toluene and co-producing light olefins in a fixed fluidized bed reactor was evaluated.

The conditions for preparing the catalyst on-line were as follows: 10 g of the formed molecular sieve sample FLHZSM-5-A prepared in Example 3 was loaded into the fixed fluidized bed reactor, first treated with 50 mL/min of nitrogen at 550° C. for 1 hour, and then cooled to 300° C. under a nitrogen atmosphere. A mixture of trimethoxyphosphine, tetraethyl silicate and toluene was fed with a micro feed pump, trimethoxyphosphine:tetraethyl silicate:toluene (weight ratio)=5:20:75. The total weight space velocity of trimethoxyphosphine, tetraethyl silicate and toluene was 1 $h^{-1}$, at atmospheric pressure. After feeding for 90 minutes, the feed was stopped, and after nitrogen purge, the temperature was raised to 550° C., and calcined in an air atmosphere for 4 hours to obtain a fluidized bed catalyst for preparing light olefins and co-producing para-xylene from methanol and toluene, which was named FLCAT-1. Then, the temperature was lowered to a reaction temperature of 450° C. under a nitrogen atmosphere, and the reaction of preparing light olefins and co-producing para-xylene from methanol and toluene was carried out. The reaction conditions were as follows: the raw materials were fed with a micro feed pump. Methanol: toluene (molar ratio) in the raw material=10:1, the total weight space velocity of methanol and toluene was 2 $h^{-1}$, at atmospheric pressure. The reaction product was analyzed by on-line Agilent 7890 gas chromatography, and the sample was analyzed at 60 min. The reaction results were shown in Table 8.

TABLE 8

| Catalyst | FLCAT-1 |
|---|---|
| Reaction Temperature (° C.) | 450 |
| Conversion Rate of Methanol (%) | 100 |
| Conversion Rate of Toluene (%) | 31.33 |
| Selectivity of Para-xylene in Xylene Isomers (wt %) | 99.61 |
| Product Distribution (wt %) | |
| Chain Hydrocarbon | 76.56 |
| Benzene | 0.09 |
| Ethylbenzene | 0.31 |
| Para-xylene | 20.25 |
| M-xylene | 0.05 |
| O-xylene | 0.03 |
| $C_{9+}$ Aromatic Hydrocarbon | 2.71 |
| Distribution of chain hydrocarbon products (wt %) | |
| $CH_4$ | 1.37 |

TABLE 8-continued

| Catalyst | FLCAT-1 |
|---|---|
| $C_2H_4$ | 40.78 |
| $C_2H_6$ | 0.12 |
| $C_3H_6$ | 35.72 |
| $C_3H_8$ | 1.5 |
| $C_4$ | 11.94 |
| $C_5$ | 4.52 |
| $C_{6+}$ | 4.05 |
| $C_2H_4 + C_3H_6$ | 76.50 |

Example 13: Preparation and Reaction Evaluation of Catalyst FXCAT-8 for Fixed Bed A fixed bed microreactor was used to produce light olefins and co-produce para-xylene using methanol and toluene as the raw material.

The conditions for preparing the catalyst in-situ were as follows: 5 g of (40 to 60 mesh) formed molecular sieve sample FXHZSM-5-A was loaded into the fixed bed microreactor, first treated with 50 mL/min of nitrogen at 550° C. for 1 hour, and then cooled to 300° C. under a nitrogen atmosphere. A mixture of trimethoxyphosphine, tetraethyl silicate and toluene was fed with a micro feed pump, trimethoxyphosphine:tetraethyl silicate:toluene (weight ratio)=5:20:75. The total weight space velocity of trimethoxyphosphine, tetraethyl silicate and toluene was 1 $h^{-1}$, at atmospheric pressure. After feeding for 90 minutes, the feed was stopped, and after nitrogen purge, the temperature was raised to 550° C., and calcined in an air atmosphere for 4 hours to obtain a fixed bed catalyst for preparing light olefins and co-producing para-xylene from methanol and toluene, which was named FXCAT-8. Then, the temperature was lowered to a reaction temperature of 450° C. under a nitrogen atmosphere, and the reaction of preparing light olefins and co-producing para-xylene from methanol and toluene was carried out. The reaction conditions were as follows: the raw materials were fed with a micro feed pump. Methanol: toluene (molar ratio) in the raw material=10:1, the total weight space velocity of methanol and toluene was 2 $h^{-1}$, at atmospheric pressure. The reaction product was analyzed by on-line Agilent 7890 gas chromatography, and the sample was analyzed at 120 min. The reaction results were shown in Table 9.

TABLE 9

| Catalyst | FXCAT-8 |
|---|---|
| Reaction Temperature (° C.) | 450 |
| Conversion Rate of Methanol (%) | 100 |
| Conversion Rate of Toluene (%) | 35.20 |
| Selectivity of ($C_2H_4 + C_3H_6$) in Chain Hydrocarbon Products (wt %) | 73.55 |
| Selectivity of Para-xylene in Xylene Isomers (wt %) | 99.71 |
| Distribution of Hydrocarbon Products (wt %) | |
| $CH_4$ | 0.84 |
| $C_2H_4$ | 30.09 |
| $C_2H_6$ | 0.08 |
| $C_3H_6$ | 25.84 |
| $C_3H_8$ | 0.90 |
| $C_4$ olefin | 9.25 |
| $C_4$ alkane | 1.55 |
| $C_{5+}$ Chain Hydrocarbon | 7.49 |
| Benzene | 0.09 |
| Ethylbenzene | 0.35 |
| Para-xylene | 20.33 |
| M-xylene | 0.04 |

TABLE 9-continued

| Catalyst | FXCAT-8 |
|---|---|
| O-xylene | 0.02 |
| $C_{9+}$ Aromatic Hydrocarbon | 3.14 |

Example 14: Preparation and Reaction of Catalyst FXCAT-9 for Fixed Bed

According to one embodiment of the present application, as shown in FIG. 1, material stream I comprises methanol and toluene, and methanol and toluene were used as the raw material to prepare light olefins and co-produce para-xylene.

The reaction system was charged with 5 g (40 to 60 mesh) of the formed molecular sieve sample FXHZSM-5-A prepared in Example 1, which was first treated with 50 mL/min of nitrogen at 550° C. for 1 hour, and then cooled to 300° C. under a nitrogen atmosphere. A mixture of trimethoxyphosphine, tetraethyl silicate and toluene was fed with a micro feed pump, trimethoxyphosphine:tetraethyl silicate:toluene (weight ratio)=5:20:75. The total weight space velocity of trimethoxyphosphine, tetraethyl silicate and toluene was 1 $h^{-1}$, at atmospheric pressure. After feeding for 90 minutes, the feed was stopped, and after nitrogen purge, the temperature was raised to 550° C., and calcined in an air atmosphere for 4 hours to obtain a fixed bed catalyst for preparing light olefins and co-producing para-xylene from methanol and toluene, which was named FXCAT-9.

The material stream I was fed to the reaction system and contacted with the catalyst FXCAT-9 and reacted. The material stream II containing the product deviated from the reaction system, and entered into the separation system. The light olefins (ethylene and propylene), $C_4$ olefins, para-xylene and other components were separated. Among them, $C_4$ olefins were returned to the reaction system, and light olefins (ethylene and propylene) and para-xylene were used as products. Other components were used as by-products.

The reaction conditions were as follows: the raw materials were fed with a micro feed pump. Methanol: toluene (molar ratio) in the material stream I=10:1, the total weight space velocity of methanol and toluene was 2 $h^{-1}$, and the reaction temperature was 450° C., at atmospheric pressure. The reaction product was analyzed by on-line Agilent 7890 gas chromatography, as shown in Table 10.

TABLE 10

| Catalyst | FXCAT-9 |
|---|---|
| Reaction Temperature (° C.) | 450 |
| Conversion Rate of Methanol (%) | 100 |
| Conversion Rate of Toluene (%) | 37.01 |
| Selectivity of ($C_2H_4$ + $C_3H_6$) in Chain Hydrocarbon Products (wt %) | 82.19 |
| Selectivity of Para-xylene in Xylene Isomers (wt %) | 99.62 |
| Distribution of Hydrocarbon Products (wt %) | |
| $CH_4$ | 0.99 |
| $C_2H_4$ | 31.87 |
| $C_2H_6$ | 0.19 |
| $C_3H_6$ | 27.54 |
| $C_3H_8$ | 1.87 |
| $C_4$ alkane | 1.62 |
| $C_{5+}$ Chain Hydrocarbon | 8.2 |
| Benzene | 0.58 |
| Ethylbenzene | 0.46 |
| Para-xylene | 23.1 |
| M-xylene | 0.05 |
| O-xylene | 0.03 |
| $C_{9+}$ Aromatic Hydrocarbon | 3.5 |

Example 15: Preparation and Reaction of Catalyst FXCAT-10 for Fixed Bed

Figure 2:
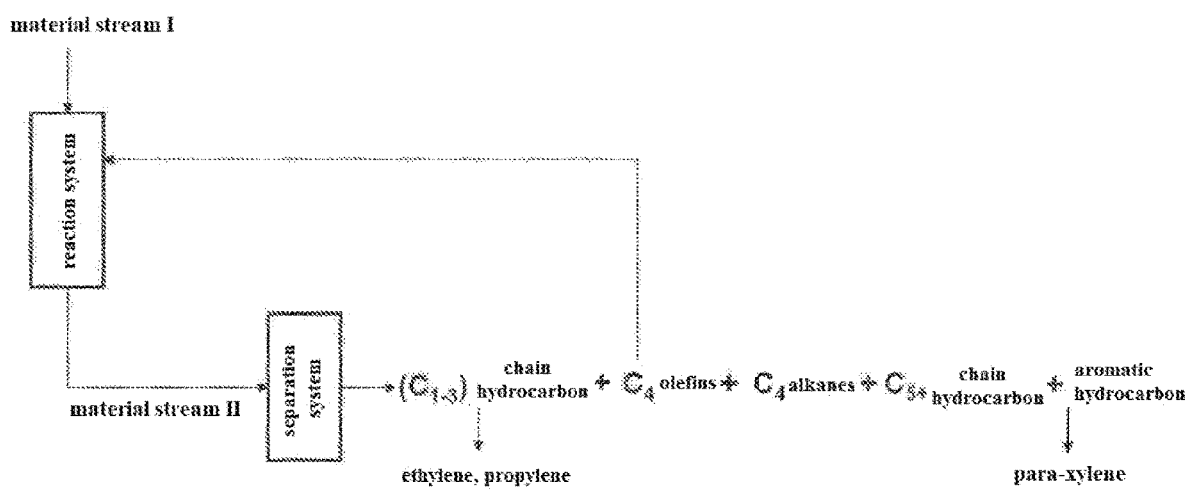
FIG. 2 is a process flow diagram of an embodiment of the application of the present application.

According to one embodiment of the present application, as shown in FIG. 2, the material stream I comprises dimethyl ether and toluene, and dimethyl ether and toluene were used as the raw material to prepare light olefins and co-produce para-xylene.

The difference from Example 14 was the separation system, and the rest was the same as in Example 14. The fixed bed catalyst was named FXCAT-10. $C_{1-3}$ chain hydrocarbons, $C_4$ olefins, $C_4$ alkanes, $C_{5+}$ chain hydrocarbons and aromatic hydrocarbons was separated from the separation system of this Example. $C_4$ olefins were returned to the reaction system. Ethylene and propylene as light olefins products were separated from $C_{1-3}$ chain hydrocarbons. Para-xylene as a product was separated from the aromatic hydrocarbons. Other components were used as by-products. The reaction results were consistent with Example 14 (the deviation was not more than ±1%).

Figure 3:
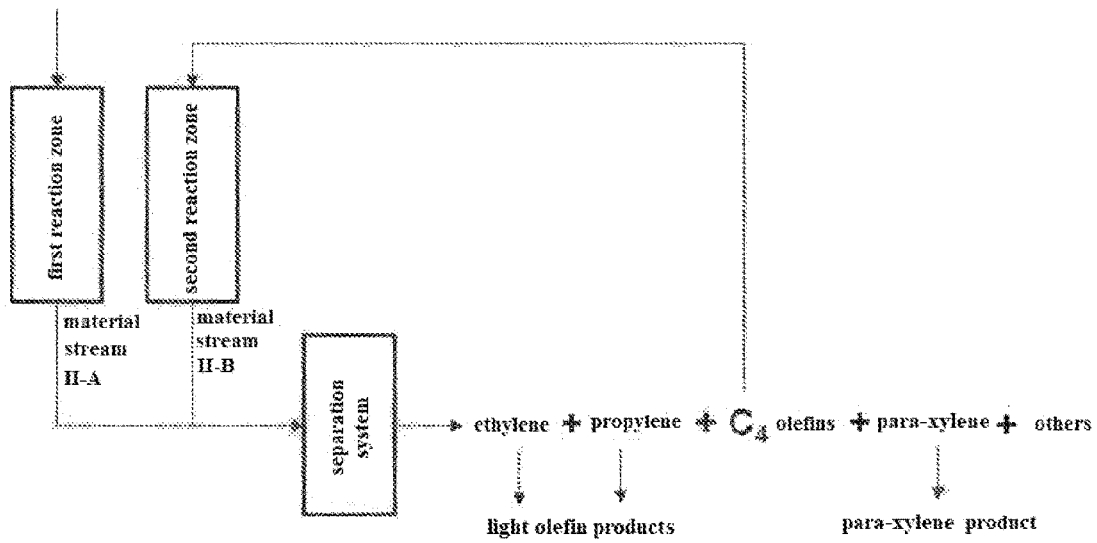
FIG. 3 is a process flow diagram of an embodiment of the application of the present application.

Example 16: Preparation and Reaction of Catalyst FXCAT-11 for Fixed Bed and Catalyst FLCAT-12 for Fluidized Bed According to one embodiment of the present application, according to the process flow diagram shown in FIG. 3, the material stream I comprises methanol and toluene, and methanol and toluene were used as the raw material to prepare light olefins and co-produce para-xylene.

The first reaction zone contained 10 fixed beds in parallel, and the second reaction zone was a fluidized bed.

50 g (40 to 60 mesh) of the formed molecular sieve sample FXHZSM-5-A prepared in Example 1 was loaded into 10 fixed beds in the first reaction zone, and each fixed bed was filled with 5 g, and each fixed bed was firstly treated with 50 mL/min of nitrogen at 550° C. for 1 hour, and then cooled to 300° C. under a nitrogen atmosphere. A mixture of trimethoxyphosphine, tetraethyl silicate and toluene was fed with a micro feed pump, trimethoxyphosphine:tetraethyl silicate:toluene (weight ratio)=5:20:75. The total weight space velocity of trimethoxyphosphine, tetraethyl silicate and toluene was 1 $h^{-1}$, at atmospheric pressure. After feeding for 90 minutes, the feed was stopped, and after nitrogen purge, the temperature was raised to 550° C., and calcined in an air atmosphere for 4 hours to obtain a fixed bed catalyst for preparing light olefins and co-producing para-xylene from methanol and toluene, which was named FXCAT-11.

50 g (40 to 60 mesh) of the formed molecular sieve sample FLHZSM-5-B prepared in Example 4 was loaded into the fluidized bed in the second reaction zone, first treated with 50 mL/min of nitrogen at 550° C. for 1 hour, and then cooled to 200° C. under a nitrogen atmosphere. A mixture of tetraethyl silicate and methanol was fed with a micro feed pump, vaporized and then fed into the fluidized bed of the second reaction zone, tetraethyl silicate:methanol (weight ratio)=40:60. The total weight space velocity of tetraethyl silicate and methanol was 2 $h^{-1}$, at atmospheric pressure. After feeding for 3 hours, the feed was stopped, and after nitrogen purge, the temperature was raised to 550° C., and calcined in an air atmosphere for 4 hours to obtain a fixed bed catalyst for preparing light olefins and co-producing para-xylene from methanol and toluene, which was named FLCAT-12.

The first reaction zone was subjected to a conversion reaction of methanol and an alkylation reaction of toluene with methanol, under the following conditions: the raw materials were fed with a micro feed pump. Methanol: toluene (molar ratio) in the raw material=10:1, the total weight space velocity of methanol and toluene was 2 h$^{-1}$, and the reaction temperature was 450° C., at atmospheric pressure. The material stream I was fed to the fixed bed of the first reaction zone and contacted with catalyst FXCAT-11 to obtain the material stream II-A, the material stream II-A deviated from the first reaction zone and entered the separation system. Ethylene, propylene, $C_4$ olefins and para-xylene were separated from the separation system. $C_4$ olefins separated from the separation system was fed into the fluidized bed of the second reaction zone to be contacted with the catalyst FXCAT-12, and the second reaction zone is subjected to the shape-selective aromatization reaction for the fluidized bed at a reaction temperature of 450° C. The material stream II-B was obtained in the second reaction zone, and the material stream II-B deviated from the second reaction zone and entered the separation system. Ethylene and propylene separated from the separation system were used as light olefins products and para-xylene was used as the product. Other components were used as by-products.

The hydrocarbon product of the second reaction zone was analyzed by on-line Agilent 7890 gas chromatography as shown in Table 11; the product distribution after deducting the component of $C_4$ olefins was shown in Table 12. The mixed hydrocarbon products from first reaction zone and the second reaction zone were analyzed by on-line Agilent 7890 gas chromatography, and the product distribution after deducting the component of $C_4$ olefins was shown in Table 13.

TABLE 11

| | |
|---|---|
| Conversion Rate of $C_4$ olefin (%) | 83.25 |
| Selectivity of Para-xylene in Xylene Isomers (wt %) | 99.56 |
| Distribution of Hydrocarbon Products (wt %) | |
| $CH_4$ | 0.74 |
| $C_2H_4$ | 0.60 |
| $C_2H_6$ | 1.02 |
| $C_3H_6$ | 0.26 |
| $C_3H_8$ | 9.55 |
| $C_4$ olefin | 16.76 |
| $C_4$ alkane | 0.04 |
| $C_{5+}$ | 0.23 |
| Benzene | 4.94 |
| Toluene | 35.74 |
| Ethylbenzene | 0.90 |
| Para-xylene | 27.07 |
| M-xylene | 0.07 |
| O-xylene | 0.05 |
| $C_{9+}$ Aromatic Hydrocarbon | 2.03 |

TABLE 12

| | |
|---|---|
| Conversion Rate of $C_4$ olefin (%) | 83.25 |
| Selectivity of Para-xylene in Xylene Isomers (wt %) | 99.56 |
| Distribution of Hydrocarbon Products (wt %) | |
| $CH_4$ | 0.89 |
| $C_2H_4$ | 0.72 |
| $C_2H_6$ | 1.22 |

TABLE 12-continued

| | |
|---|---|
| $C_3H_6$ | 0.31 |
| $C_3H_8$ | 11.47 |
| $C_4$ alkane | 0.05 |
| $C_{5+}$ Chain Hydrocarbon | 0.28 |
| Benzene | 5.93 |
| Toluene | 42.94 |
| Ethylbenzene | 1.08 |
| Para-xylene | 32.52 |
| M-xylene | 0.08 |
| O-xylene | 0.06 |
| $C_{9+}$ Aromatic Hydrocarbon | 2.44 |

TABLE 13

| | |
|---|---|
| Conversion Rate of Methanol (%) | 100 |
| Conversion Rate of Toluene (%) | 38.08 |
| Selectivity of ($C_2H_4$ + $C_3H_6$) in Chain Hydrocarbon Products (wt %) | 82.44 |
| Selectivity of Para-xylene in Xylene Isomers (wt %) | 99.69 |
| Distribution of Hydrocarbon Products (wt %) | |
| $CH_4$ | 0.94 |
| $C_2H_4$ | 31.68 |
| $C_2H_6$ | 0.19 |
| $C_3H_6$ | 27.18 |
| $C_3H_8$ | 1.85 |
| $C_4$ alkane | 1.64 |
| $C_{5+}$ Chain Hydrocarbon | 7.90 |
| Benzene | 0.58 |
| Ethylbenzene | 0.46 |
| Para-xylene | 24.00 |
| M-xylene | 0.05 |
| O-xylene | 0.03 |
| $C_{9+}$ Aromatic Hydrocarbon | 3.50 |

Example 17: Preparation and Reaction of Catalyst FXCAT-13 and Catalyst FLCAT-14

Figure 4:
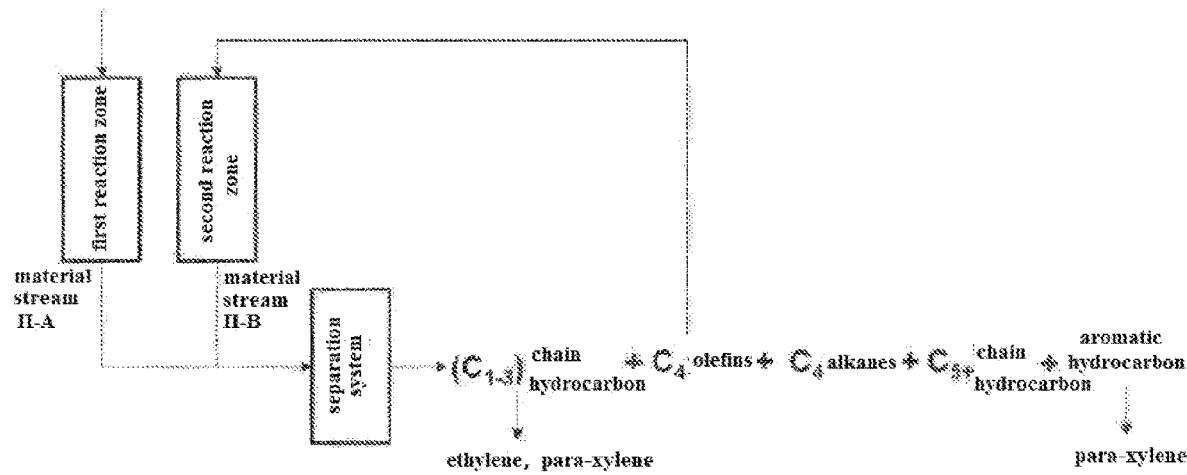
FIG. 4 is a process flow diagram of an embodiment of the application of the present application.

According to one embodiment of the present application, as shown in FIG. 4, the material stream I comprises dimethyl ether, methanol and toluene, and dimethyl ether, methanol and toluene were used as the raw material to prepare light olefins and co-produce para-xylene.

The difference from Example 16 was that the first reaction zone contained one fixed bed filled with 50 g of molecular sieve sample FXHZSM-5-A. The difference was also the separation system. $C_{1\sim3}$ chain hydrocarbons, $C_4$ olefins, $C_4$ alkanes, $C_{5+}$ chain hydrocarbons and aromatic hydrocarbons were separated from the separation system of this Example. $C_4$ olefins were returned to the second reaction zone. Ethylene and propylene as light olefins products were separated from $C_{1\sim3}$ chain hydrocarbons. Para-xylene as a product was separated from the aromatic hydrocarbons. Other components were used as by-products. The rest was the same as in Example 23, and the fixed bed catalyst was designated as FXCAT-13, and the fluidized bed catalyst was designated as FLCAT-14. The reaction results were consistent with that of Example 16 (the deviation was not more than ±1%).

Example 18: Preparation and Reaction of Catalyst FXCAT-15 for Fixed Bed

Figure 5:
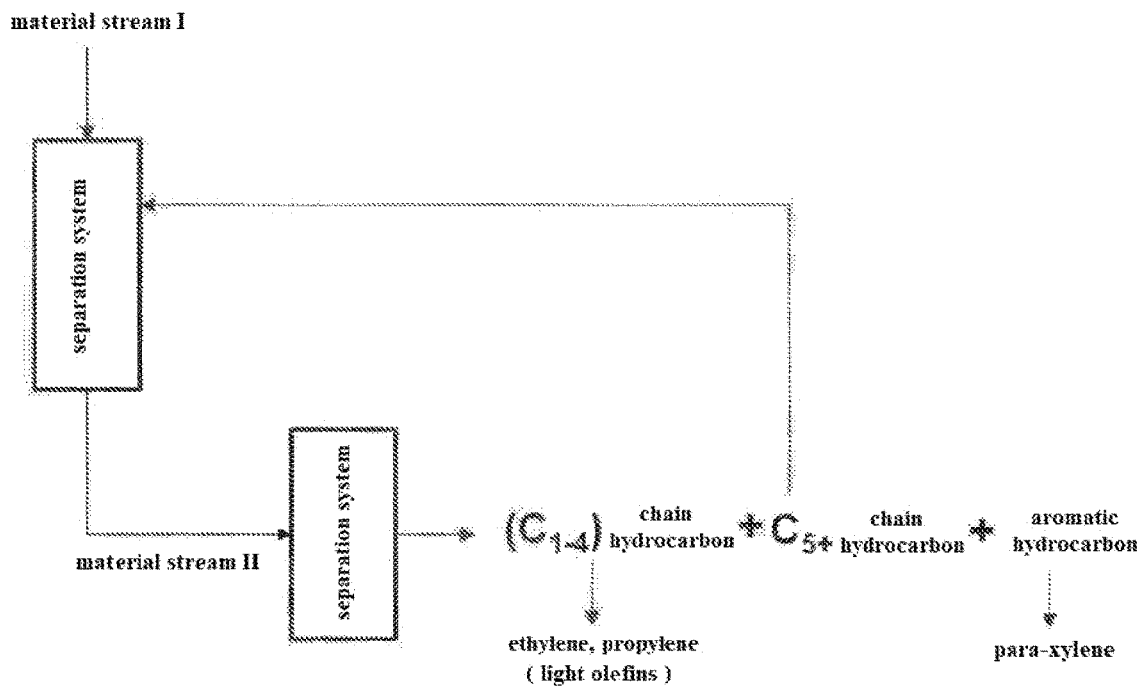
FIG. 5 is a process flow diagram of an embodiment of the application of the present application.

According to one embodiment of the present application, as per the process flow diagram shown in FIG. 5, methanol and toluene were used as the raw material to prepare light olefins and co-produce para-xylene. The material stream I comprises methanol and toluene.

The reaction system was two fixed beds. As shown in FIG. 5, parts of the reaction system were arranged in series above and below. Using a staged feed, the material stream I was fed from the upper fixed bed and the recirculated $C_{5+}$ chain hydrocarbons entered the lower fixed bed.

10 g (40 to 60 mesh) of the formed molecular sieve sample FXHZSM-5-A prepared in Example 1 was separately loaded into two fixed beds, and the two fixed bed loadings were the same, both being 5 g. The preparation process of catalyst was as follows: each fixed bed was firstly treated with 50 mL/min of nitrogen at 550° C. for 1 hour, and then cooled to 300° C. under a nitrogen atmosphere. A mixture of trimethoxyphosphine, tetraethyl silicate and toluene was fed with a micro feed pump, trimethoxyphosphine:tetraethyl silicate:toluene (weight ratio)=5:20:75. The total weight space velocity of trimethoxyphosphine, tetraethyl silicate and toluene was $1\ h^{-1}$, at atmospheric pressure. After feeding for 90 minutes, the feed was stopped, and after nitrogen purge, the temperature was raised to 550° C., and calcined in an air atmosphere for 4 hours to prepare a fixed bed catalyst in-situ for preparing light olefins and co-producing para-xylene from methanol and toluene, which was named FXCAT-15.

The material stream I entered the fixed bed reactor in the upper part of the reaction system, contacted with the catalyst FXCAT-15, and was subjected to a conversion reaction of methanol and a shape-selective alkylation reaction of toluene and methanol. The reaction conditions were as follows: the raw materials were fed with a micro feed pump. Methanol: toluene (molar ratio) in the raw material=10:1, the total weight space velocity of methanol and toluene was $2\ h^{-1}$, and the reaction temperature was 450° C., at atmospheric pressure.

The material stream II containing product deviated from the reaction system and entered the separation system to separate $C_{1-4}$ chain hydrocarbons, $C_{5+}$ chain hydrocarbons and aromatic hydrocarbons. Among them, the $C_{5+}$ chain hydrocarbons were returned to the fixed bed in the lower part of the reaction system, and was contacted with the catalyst FXCAT-15 to carry out a reaction such as pyrolysis and shape-selective aromatization, and the reaction temperature of the fixed bed in the lower part of the reaction system was 630° C. Ethylene and propylene as light olefins products were separated from $C_{1-4}$ chain hydrocarbons. Para-xylene as a product was separated from the aromatic hydrocarbon. Other components were used as by-products.

The product was analyzed by on-line Agilent 7890 gas chromatography as shown in Table 14.

TABLE 14

| | |
|---|---|
| Conversion Rate of Methanol (%) | 100 |
| Conversion Rate of Toluene (%) | 36.55 |
| Selectivity of ($C_2H_4$ + $C_3H_6$) in Chain Hydrocarbon Products | 80.83 |
| Selectivity of Para-xylene in Xylene Isomers (wt %) | 99.70 |
| Distribution of Hydrocarbon Products (wt %) | |
| $CH_4$ | 1.11 |
| $C_2H_4$ | 33.02 |
| $C_2H_6$ | 0.31 |
| $C_3H_6$ | 27.25 |
| $C_3H_8$ | 1.17 |
| $C_4$ | 11.7 |
| Benzene | 0.65 |
| Ethylbenzene | 0.39 |
| Para-xylene | 21.05 |
| M-xylene | 0.04 |

TABLE 14-continued

| | |
|---|---|
| O-xylene | 0.02 |
| $C_{9+}$ Aromatic Hydrocarbon | 3.29 |

Example 19: Preparation and Reaction of Catalyst FXCAT-16 for Fixed Bed

Figure 6:
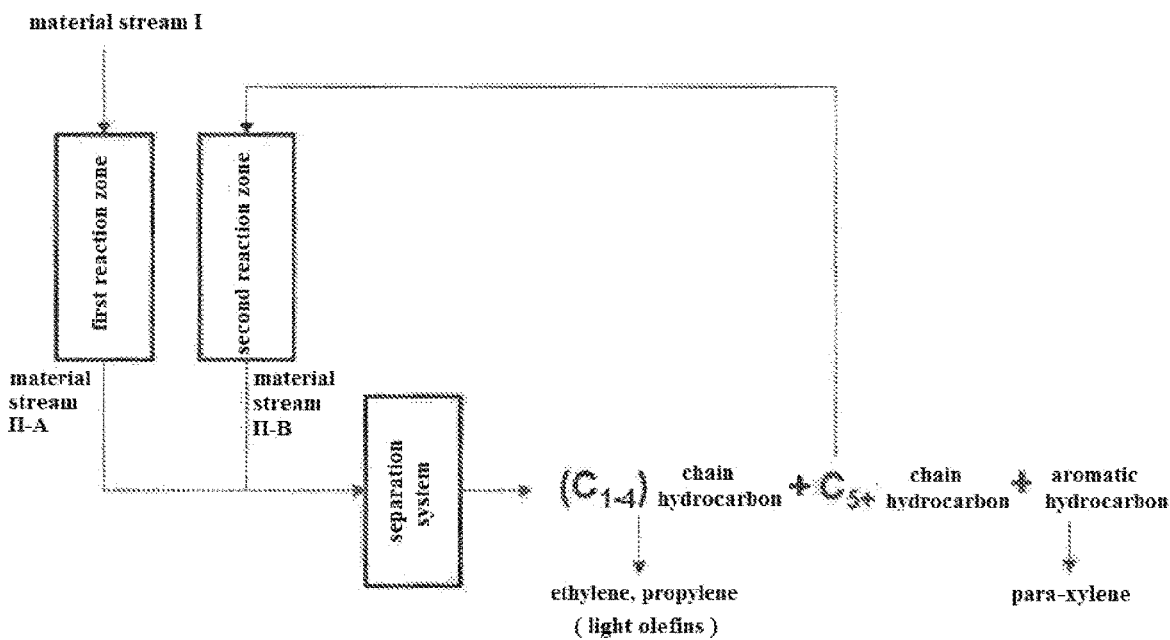
FIG. 6 is a process flow diagram of an embodiment of the application of the present application.

According to one embodiment of the present application, according to the process flow diagram shown in FIG. 6, methanol and toluene were used as the raw material to prepare light olefins and co-produce para-xylene. The material stream I comprises methanol and toluene.

The first reaction zone contained one fixed bed, and the second reaction zone contained one fixed bed.

5 g (40 to 60 mesh) of the formed molecular sieve sample FXHZSM-5-A prepared in Example 1 was separately loaded into a fixed bed of the first reaction zone and a fixed bed of the second reaction zone. The preparation process of the catalyst was the same: the catalyst in each fixed bed was treated with 50 mL/min of nitrogen at 550° C. for 1 hour, and then cooled to 300° C. under a nitrogen atmosphere. A mixture of trimethoxyphosphine, tetraethyl silicate and toluene was fed with a micro feed pump, trimethoxyphosphine:tetraethyl silicate:toluene (weight ratio)=5:20:75. The total weight space velocity of trimethoxyphosphine, tetraethyl silicate and toluene was $1\ h^{-1}$, at atmospheric pressure. After feeding for 90 minutes, the feed was stopped, and after nitrogen purge, the temperature was raised to 550° C., and calcined in an air atmosphere for 4 hours. According to the above process, the fixed bed catalyst for preparing light olefins from methanol and toluene and co-producing para-xylene, was in-situ prepared in the first fixed bed reaction zone and the second fixed bed reaction zone, respectively, and recorded as FXCAT-16.

The material stream I entered the fixed bed of the first reaction zone and contacted with the catalyst FXCAT-16, and was subjected to a conversion reaction of methanol and a shape-selective alkylation reaction of toluene and methanol. The reaction conditions were as follows: the raw materials were fed with a micro feed pump. Methanol: toluene (molar ratio) in the raw material=10:1, the total weight space velocity of methanol and toluene was $2\ h^{-1}$, and the reaction temperature was 450° C., at atmospheric pressure. The material stream II-A containing product deviated from the fixed bed of the first reaction zone and entered the separation system to separate $C_{1-4}$ chain hydrocarbons, $C_{5+}$ chain hydrocarbons and aromatic hydrocarbons from the separation system.

The $C_{5+}$ chain hydrocarbons separated from the separation system were returned to the fixed bed of the second reaction zone, and were contacted with the catalyst FXCAT-16 to carry out a reaction such as pyrolysis and shape-selective aromatization, and the reaction temperature of the fixed bed of the second reaction zone was 630° C. The material stream II-B containing the product exited the fixed bed of the second reaction zone and entered the separation system. Ethylene and propylene, as light olefins products, from the separation system, were separated from $C_{1-4}$ chain hydrocarbons. Para-xylene as a product was separated from the aromatic hydrocarbon. Other components were used as by-products.

The hydrocarbon product of the second reaction zone was analyzed by on-line Agilent 7890 gas chromatography as shown in Table 15; the product distribution after deducting the component of $C_{5+}$ chain hydrocarbons was shown in Table 16. The mixed hydrocarbon products from first reaction zone and the second reaction zone were analyzed by on-line Agilent 7890 gas chromatography, and the product distribution after deducting the component of $C_{5+}$ chain hydrocarbons was shown in Table 17.

TABLE 15

| | |
|---|---|
| Conversion Rate of $C_{5+}$ Chain Hydrocarbon (%) | 93.92 |
| Selectivity of Para-xylene in Xylene Isomers (wt %) | 99.70 |
| Distribution of Hydrocarbon Products (wt %) | |
| $CH_4$ | 4.32 |
| $C_2H_4$ | 20.83 |
| $C_2H_6$ | 3.02 |
| $C_3H_6$ | 23.37 |
| $C_3H_8$ | 3.45 |
| $C_4$ | 8.51 |
| $C_{5+}$ | 6.08 |
| Benzene | 7.46 |
| Toluene | 11.07 |
| Ethylbenzene | 0.52 |
| Para-xylene | 9.96 |
| M-xylene | 0.03 |
| O-xylene | 0.02 |
| $C_{9+}$ Aromatic Hydrocarbon | 1.36 |

TABLE 16

| | |
|---|---|
| Conversion Rate of $C_{5+}$ Chain Hydrocarbon (%) | 93.92 |
| Selectivity of Para-xylene in Xylene Isomers (wt %) | 99.70 |
| Distribution of Hydrocarbon Products (wt %) | |
| $CH_4$ | 4.60 |
| $C_2H_4$ | 22.18 |
| $C_2H_6$ | 3.22 |
| $C_3H_6$ | 24.88 |
| $C_3H_8$ | 3.67 |
| $C_4$ | 9.06 |
| Benzene | 7.94 |
| Toluene | 11.79 |
| Ethylbenzene | 0.55 |
| Para-xylene | 10.60 |
| M-xylene | 0.03 |
| O-xylene | 0.02 |
| $C_{9+}$ Aromatic Hydrocarbon | 1.45 |

TABLE 17

| | |
|---|---|
| Conversion Rate of Methanol (%) | 100 |
| Conversion Rate of Toluene (%) | 37.11 |
| Selectivity of ($C_2H_4$ + $C_3H_6$) in Chain Hydrocarbon Products | 80.81 |
| Selectivity of Para-xylene in Xylene Isomers (wt %) | 99.70 |
| Distribution of Hydrocarbon Products (wt %) | |
| $CH_4$ | 1.18 |
| $C_2H_4$ | 32.06 |
| $C_2H_6$ | 0.31 |
| $C_3H_6$ | 27.95 |
| $C_3H_8$ | 1.17 |
| $C_4$ | 11.59 |
| Benzene | 0.65 |
| Ethylbenzene | 0.39 |
| Para-xylene | 21.35 |
| M-xylene | 0.04 |
| O-xylene | 0.02 |
| $C_{9+}$ Aromatic Hydrocarbon | 3.29 |

Example 20: Preparation and Reaction of Catalyst FXCAT-17 for Fluidized Bed

According to one embodiment of the present application, the flowchart was the same as that of Example 19, as shown in FIG. 6. The difference was in the raw materials and reactors.

The material stream I in this Example comprises dimethyl ether, methanol and toluene, and dimethyl ether, methanol and toluene were used as the raw material to prepare light olefins and co-produce para-xylene.

In the Example, the first reaction zone was one fluidized bed packed with 1 kg of the molecular sieve sample FLHZSM-5-C in Example 4. The second reaction zone was one fluidized bed packed with 1 kg of the same molecular sieve sample FLHZSM-5-C in Example 4. The preparation process of catalyst was as follows: the catalyst in each fluidized bed reactor was treated with 50 mL/min of nitrogen at 550° C. for 1 hour, and then cooled to 300° C. under a nitrogen atmosphere. The rest was the same as in Example 19, and the fixed bed catalyst was designated as FLCAT-17. The reaction results were consistent with Example 19 (the deviation was not more than ±1%).

Example 21: Preparation and Reaction Evaluation of Catalyst FXCAT-18 for Fixed Bed The reaction performance of on-line preparing fixed bed catalyst for preparing toluene and co-producing para-xylene by alkylation from methanol and/or dimethyl ether and benzene in a fixed bed microreactor was evaluated.

The conditions for preparing the catalyst on-line were as follows: 5 g of (40 to 60 mesh) formed molecular sieve sample FXHZSM-5-C was loaded into the fixed bed reactor, first treated with 50 mL/min of air at 550° C. for 1 hour, and then cooled to 200° C. under a nitrogen atmosphere. Tetraethyl silicate was fed with a micro feed pump. The weight space velocity of tetraethyl silicate was 0.2 $h^{-1}$, at atmospheric pressure. After feeding for 1 hour, the feed was stopped, and after nitrogen purge, the temperature was raised to 550° C., and calcined in an air atmosphere for 4 hours. The temperature was raised to 700° C. under a nitrogen atmosphere, and the water was fed with a micro feed pump, at a water weight space velocity of 2 $h^{-1}$ and atmospheric pressure. After feeding for 4 hours, the feed was stopped to obtain a fixed bed catalyst for preparing toluene and co-producing para-xylene by alkylation from methanol and/or dimethyl ether and benzene, which was named FXCAT-18. Then, the reaction temperature was cooled to 450° C. under a nitrogen atmosphere to test the reaction of preparing toluene and co-producing para-xylene by alkylation from methanol and/or dimethyl ether and benzene. The reaction conditions were as follows: the raw materials were fed with a micro feed pump. Benzene:methanol (molar ratio) in the raw material=1:1, the total weight space velocity of benzene and methanol was 2 $h^{-1}$, at atmospheric pressure. The reaction product was analyzed by on-line Agilent 7890 gas chromatography, and the sample was analyzed at 120 min. The reaction results were shown in Table 18.

TABLE 18

| Catalyst | FXCAT-18 |
|---|---|
| Reaction Temperature (° C.) | 450 |
| Conversion Rate of Methanol (%) | 100 |
| Conversion Rate of Toluene (%) | 35.93 |

TABLE 18-continued

| Catalyst | FXCAT-18 |
|---|---|
| Selectivity of Para-xylene in Xylene Products (wt %) | 99.63 |
| Selectivity of Para-xylene in $C_8$ Aromatic Products (wt %) | 91.06 |
| Selectivity of (Toluene + Para-xylene) in Aromatic Products (wt %) | 94.16 |
| Distribution of Products (wt %) | |
| $C_1$-$C_{6+}$ Chain Hydrocarbon | 14.72 |
| Toluene | 53.09 |
| Ethylbenzene | 2.57 |
| Para-xylene | 27.21 |
| M-xylene | 0.06 |
| O-xylene | 0.04 |
| $C_{9+}$ Aromatic Hydrocarbon | 2.31 |

Example 22: Preparation and Reaction Evaluation of Catalyst FXCAT-19 for Fixed Bed The reaction performance of on-line preparing fixed bed catalyst for preparing toluene and co-producing para-xylene by alkylation from methanol and/or dimethyl ether and benzene in a fixed bed microreactor was evaluated.

The conditions for preparing the catalyst on-line were as follows: 5 g of (40 to 60 mesh) formed molecular sieve sample FXHZSM-5-C was loaded into the fixed bed reactor, first treated with 50 mL/min of air at 550° C. for 1 hour, and then cooled to 200° C. under a nitrogen atmosphere. Tetraethyl silicate was fed with a micro feed pump. The weight space velocity of tetraethyl silicate was 0.1 $h^{-1}$, at atmospheric pressure. After feeding for 2 hours, the feed was stopped, and after nitrogen purge, the temperature was raised to 550° C., and calcined in an air atmosphere for 4 hours. The temperature was raised to 700° C. under a nitrogen atmosphere, and the water was fed with a micro feed pump, at a water weight space velocity of 2 $h^{-1}$ and atmospheric pressure. After feeding for 4 hours, the feed was stopped to obtain a fixed bed catalyst for preparing toluene and co-producing para-xylene by alkylation from methanol and/or dimethyl ether and benzene, which was named FXCAT-19. Then, the reaction temperature was cooled to 450° C. under a nitrogen atmosphere to test the reaction of preparing toluene and co-producing para-xylene by alkylation from methanol and/or dimethyl ether and benzene. The reaction conditions were as follows: the raw materials were fed with a micro feed pump. Benzene:methanol (molar ratio) in the raw material=1:1, the total weight space velocity of benzene and methanol was 2 $h^{-1}$, at atmospheric pressure. The reaction product was analyzed by on-line Agilent 7890 gas chromatography, and the sample was analyzed at 120 min. The reaction results were shown in Table 19.

TABLE 19

| Catalyst | FXCAT-19 |
|---|---|
| Reaction Temperature (° C.) | 450 |
| Conversion Rate of Methanol (%) | 100 |
| Conversion Rate of Toluene (%) | 35.43 |
| Selectivity of Para-xylene in Xylene Products (wt %) | 99.78 |
| Selectivity of Para-xylene in $C_8$ Aromatic Products (wt %) | 91.33 |
| Selectivity of (Toluene + Para-xylene) in Aromatic Products (wt %) | 94.37 |
| Distribution of Products (wt %) | |
| $C_1$-$C_{6+}$ Chain Hydrocarbon | 14.81 |

TABLE 19-continued

| Catalyst | FXCAT-19 |
|---|---|
| Toluene | 53.32 |
| Ethylbenzene | 2.51 |
| Para-xylene | 27.07 |
| M-xylene | 0.04 |
| O-xylene | 0.02 |
| $C_{9+}$ Aromatic Hydrocarbon | 2.23 |

Example 23: Preparation and Reaction Evaluation of Catalyst FXCAT-20 for Fixed Bed The reaction performance of on-line preparing fixed bed catalyst for preparing toluene and co-producing para-xylene by alkylation from methanol and/or dimethyl ether and benzene in a fixed bed microreactor was evaluated.

The conditions for preparing the catalyst on-line were as follows: 5 g of (40 to 60 mesh) formed molecular sieve sample FXHZSM-5-C was loaded into the fixed bed reactor, first treated with 50 mL/min of air at 550° C. for 1 hour, and then cooled to 200° C. under a nitrogen atmosphere. Tetraethyl silicate was fed with a micro feed pump. The weight space velocity of tetraethyl silicate was 0.4 $h^{-1}$, at atmospheric pressure. After feeding for 0.5 hour, the feed was stopped, and after nitrogen purge, the temperature was raised to 550° C., and calcined in an air atmosphere for 4 hours. The temperature was raised to 700° C. under a nitrogen atmosphere, and the water was fed with a micro feed pump, at a water weight space velocity of 2 $h^{-1}$ and atmospheric pressure. After feeding for 4 hours, the feed was stopped to obtain a fixed bed catalyst for preparing toluene and co-producing para-xylene by alkylation from methanol and/or dimethyl ether and benzene, which was named FXCAT-20. Then, the reaction temperature was cooled to 450° C. under a nitrogen atmosphere to test the reaction of preparing toluene and co-producing para-xylene by alkylation from methanol and/or dimethyl ether and benzene. The reaction conditions were as follows: the raw materials were fed with a micro feed pump. Benzene:methanol (molar ratio) in the raw material=1:1, the total weight space velocity of benzene and methanol was 2 $h^{-1}$, at atmospheric pressure. The reaction product was analyzed by on-line Agilent 7890 gas chromatography, and the sample was analyzed at 120 min. The reaction results were shown in Table 20.

TABLE 20

| Catalyst | FXCAT-20 |
|---|---|
| Reaction Temperature (° C.) | 450 |
| Conversion Rate of Methanol (%) | 100 |
| Conversion Rate of Benzene (%) | 36.37 |
| Selectivity of Para-xylene in Xylene Products (wt %) | 99.67 |
| Selectivity of Para-xylene in $C_8$ Aromatic Products (wt %) | 90.95 |
| Selectivity of (Toluene + Para-xylene) in Aromatic Products (wt %) | 93.99 |
| Distribution of Products (wt %) | |
| $C_1$-$C_{6+}$ Chain Hydrocarbon | 14.61 |
| Toluene | 52.92 |
| Ethylbenzene | 2.63 |
| Para-xylene | 27.34 |
| M-xylene | 0.05 |
| O-xylene | 0.04 |
| $C_{9+}$ Aromatic Hydrocarbon | 2.41 |

Example 24: Preparation and Reaction Evaluation of Catalyst FXCAT-21 for Fixed Bed The reaction performance of on-line preparing fixed bed catalyst for preparing toluene and co-producing para-xylene by alkylation from methanol and/or dimethyl ether and benzene in a fixed bed microreactor was evaluated.

The conditions for preparing the catalyst on-line were as follows: 5 g of (40 to 60 mesh) formed molecular sieve sample FXHZSM-5-C was loaded into the fixed bed reactor, first treated with 50 mL/min of air at 550° C. for 1 hour, and then cooled to 300° C. under a nitrogen atmosphere. Tetraethyl silicate was fed with a micro feed pump. The weight space velocity of tetraethyl silicate was 0.2 $h^{-1}$, at atmospheric pressure. After feeding for 1 hour, the feed was stopped, and after nitrogen purge, the temperature was raised to 550° C., and calcined in an air atmosphere for 4 hours. The temperature was raised to 700° C. under a nitrogen atmosphere, and the water was fed with a micro feed pump, at a water weight space velocity of 2 $h^{-1}$ and atmospheric pressure. After feeding for 4 hours, the feed was stopped to obtain a fixed bed catalyst for preparing toluene and co-producing para-xylene by alkylation from methanol and/or dimethyl ether and benzene, which was named FXCAT-21. Then, the reaction temperature was cooled to 450° C. under a nitrogen atmosphere to test the reaction of preparing toluene and co-producing para-xylene by alkylation from methanol and/or dimethyl ether and benzene. The reaction conditions were as follows: the raw materials were fed with a micro feed pump.

Benzene:methanol (molar ratio) in the raw material=1:1, the total weight space velocity of benzene and methanol was 2 $h^{-1}$, at atmospheric pressure. The reaction product was analyzed by on-line Agilent 7890 gas chromatography, and the sample was analyzed at 120 min. The reaction results were shown in Table 21.

TABLE 21

| Catalyst | FXCAT-21 |
| --- | --- |
| Reaction Temperature (° C.) | 450 |
| Conversion Rate of Methanol (%) | 100 |
| Conversion Rate of Benzene (%) | 35.37 |
| Selectivity of Para-xylene in Xylene Products (wt %) | 99.70 |
| Selectivity of Para-xylene in $C_8$ Aromatic Products (wt %) | 90.48 |
| Selectivity of (Toluene +Para-xylene) in Aromatic Products (wt %) | 93.09 |
| Distribution of Products (wt %) | |
| $C_1$-$C_{6+}$ Chain Hydrocarbon | 13.62 |
| Toluene | 53.41 |
| Ethylbenzene | 2.76 |
| Para-xylene | 26.99 |
| M-xylene | 0.04 |
| O-xylene | 0.04 |
| $C_{9+}$ Aromatic Hydrocarbon | 3.13 |

Example 25: Preparation and Reaction Evaluation of Catalyst FXCAT-22 for Fixed Bed The reaction performance of on-line preparing fixed bed catalyst for preparing toluene and co-producing para-xylene by alkylation from methanol and/or dimethyl ether and benzene in a fixed bed microreactor was evaluated.

The conditions for preparing the catalyst on-line were as follows: 5 g of (40 to 60 mesh) formed molecular sieve sample FXHZSM-5-C was loaded into the fixed bed reactor, first treated with 50 mL/min of air at 550° C. for 1 hour, and then cooled to 450° C. under a nitrogen atmosphere. Tetraethyl silicate was fed with a micro feed pump. The weight space velocity of tetraethyl silicate was 0.2 $h^{-1}$, at atmospheric pressure. After feeding for 1 hour, the feed was stopped, and after nitrogen purge, the temperature was raised to 550° C., and calcined in an air atmosphere for 4 hours. The temperature was raised to 700° C. under a nitrogen atmosphere, and the water was fed with a micro feed pump, at a water weight space velocity of 2 $h^{-1}$ and atmospheric pressure. After feeding for 4 hours, the feed was stopped to obtain a fixed bed catalyst for preparing toluene and co-producing para-xylene by alkylation from methanol and/or dimethyl ether and benzene, which was named FXCAT-22. Then, the reaction temperature was cooled to 450° C. under a nitrogen atmosphere to test the reaction of preparing toluene and co-producing para-xylene by alkylation from methanol and/or dimethyl ether and benzene. The reaction conditions were as follows: the raw materials were fed with a micro feed pump. Benzene:methanol (molar ratio) in the raw material=1:1, the total weight space velocity of benzene and methanol was 2 $h^{-1}$, at atmospheric pressure. The reaction product was analyzed by on-line Agilent 7890 gas chromatography, and the sample was analyzed at 120 min. The reaction results were shown in Table 22.

TABLE 22

| Catalyst | FXCAT-22 |
| --- | --- |
| Reaction Temperature (° C.) | 450 |
| Conversion Rate of Methanol (%) | 100 |
| Conversion Rate of Benzene (%) | 36.71 |
| Selectivity of Para-xylene in Xylene Products (wt %) | 99.63 |
| Selectivity of Para-xylene in $C_8$ Aromatic Products (wt %) | 90.28 |
| Selectivity of (Toluene + Para-xylene) in Aromatic Products (wt %) | 92.88 |
| Distribution of Products (wt %) | |
| $C_1$-$C_{6+}$ Chain Hydrocarbon | 13.33 |
| Toluene | 53.65 |
| Ethylbenzene | 2.79 |
| Para-xylene | 26.85 |
| M-xylene | 0.06 |
| O-xylene | 0.04 |
| $C_{9+}$ Aromatic Hydrocarbon | 3.28 |

Example 26: Preparation and Reaction Evaluation of Catalyst FXCAT-23 for Fixed Bed The reaction performance of on-line preparing fixed bed catalyst for preparing toluene and co-producing para-xylene by alkylation from methanol and/or dimethyl ether and benzene in a fixed bed microreactor was evaluated.

The conditions for preparing the catalyst on-line were as follows: 5 g of (40 to 60 mesh) formed molecular sieve sample FXHZSM-5-C was loaded into the fixed bed reactor, first treated with 50 mL/min of air at 550° C. for 1 hour, and then cooled to 300° C. under a nitrogen atmosphere. Tetraethyl silicate was fed with a micro feed pump. The weight space velocity of tetraethyl silicate was 0.2 $h^{-1}$, at atmospheric pressure. After feeding for 1 hour, the feed was stopped, and after nitrogen purge, the temperature was raised to 550° C., and calcined in an air atmosphere for 4 hours. The temperature was raised to 800° C. under a nitrogen atmosphere, and the water was fed with a micro feed pump, at a water weight space velocity of 2 $h^{-1}$ and atmospheric pressure. After feeding for 2 hours, the feed was stopped to obtain a fixed bed catalyst for preparing toluene and co-producing para-xylene by alkylation from methanol and/or dimethyl ether and benzene, which was named FXCAT-23. Then, the reaction temperature was cooled to 450° C. under a nitrogen atmosphere to test the reaction of preparing toluene and co-producing para-xylene by alkylation from methanol and/or dimethyl ether and benzene. The reaction conditions were as follows: the raw materials were fed with a micro feed pump. Benzene:methanol (molar ratio) in the raw material=1:1, the total weight space velocity of benzene and methanol was 2 $h^{-1}$, at atmospheric pressure. The reaction product was analyzed by on-line Agilent 7890 gas chromatography, and the sample was analyzed at 120 min. The reaction results were shown in Table 23.

TABLE 23

| Catalyst | FXCAT-23 |
| --- | --- |
| Reaction Temperature (° C.) | 450 |
| Conversion Rate of Methanol (%) | 100 |
| Conversion Rat eof Benzene (%) | 33.26 |
| Selectivity of Para-xylene in Xylene Products (wt %) | 99.65 |
| Selectivity of Para-xylene in $C_8$ Aromatic Products (wt %) | 91.19 |
| Selectivity of (Toluene + Para-xylene) in Aromatic Products (wt %) | 93.68 |
| Distribution of Products (wt %) | |
| $C_1$-$C_{6+}$ Chain Hydrocarbon | 14.57 |
| Toluene | 54.35 |
| Ethylbenzene | 2.39 |
| Para-xylene | 25.68 |
| M-xylene | 0.05 |
| O-xylene | 0.04 |
| $C_{9+}$ Aromatic Hydrocarbon | 2.92 |

Example 27: Preparation and Reaction Evaluation of Catalyst FXCAT-24 for Fixed Bed The reaction performance of on-line preparing fixed bed catalyst for preparing toluene and co-producing para-xylene by alkylation from methanol and/or dimethyl ether and benzene in a fixed bed microreactor was evaluated.

The conditions for preparing the catalyst on-line were as follows: 5 g of (40 to 60 mesh) formed molecular sieve sample FXHZSM-5-C was loaded into the fixed bed reactor, first treated with 50 mL/min of air at 550° C. for 1 hour, and then cooled to 300° C. under a nitrogen atmosphere. Tetraethyl silicate was fed with a micro feed pump. The weight space velocity of tetraethyl silicate was 0.2 $h^{-1}$, at atmospheric pressure. After feeding for 1 hour, the feed was stopped, and after nitrogen purge, the temperature was raised to 550° C., and calcined in an air atmosphere for 4 hours. The temperature was raised to 600° C. under a nitrogen atmosphere, and the water was fed with a micro feed pump, at a water weight space velocity of 2 $h^{-1}$ and atmospheric pressure. After feeding for 8 hours, the feed was stopped to obtain a fixed bed catalyst for preparing toluene and co-producing para-xylene by alkylation from methanol and/or dimethyl ether and benzene, which was named FXCAT-24. Then, the reaction temperature was cooled to 450° C. under a nitrogen atmosphere to test the reaction of preparing toluene and co-producing para-xylene by alkylation from methanol and/or dimethyl ether and benzene. The reaction conditions were as follows: the raw materials were fed with a micro feed pump.

Benzene:methanol (molar ratio) in the raw material=1:1, the total weight space velocity of benzene and methanol was 2 $h^{-1}$, at atmospheric pressure. The reaction product was analyzed by on-line Agilent 7890 gas chromatography, and the sample was analyzed at 120 min. The reaction results were shown in Table 24.

TABLE 24

| Catalyst | FXCAT-24 |
| --- | --- |
| Reaction Temperature (° C.) | 450 |
| Conversion Rate of Methanol (%) | 100 |
| Conversion Rate of Benzene (%) | 36.97 |
| Selectivity of Para-xylene in Xylene Products (wt %) | 99.70 |
| Selectivity of Para-xylene in $C_8$ Aromatic Products (wt %) | 91.48 |
| Selectivity of (Toluene + Para-xylene) in Aromatic Products (wt %) | 93.42 |
| Distribution of Products (wt %) | |
| $C_1$-$C_{6+}$ Chain Hydrocarbon | 14.07 |
| Toluene | 53.96 |
| Ethylbenzene | 2.37 |
| Para-xylene | 26.31 |
| M-xylene | 0.05 |
| O-xylene | 0.03 |
| $C_{9+}$ Aromatic Hydrocarbon | 3.20 |

Example 28: Preparation and Reaction Evaluation of Catalyst FXCAT-25 for Fixed Bed The reaction performance of on-line preparing fixed bed catalyst for preparing toluene and co-producing para-xylene by alkylation from methanol and/or dimethyl ether and benzene in a fixed bed microreactor was evaluated.

The conditions for preparing the catalyst on-line were as follows: 5 g of (40 to 60 mesh) formed molecular sieve sample FXHZSM-11-B was loaded into the fixed bed reactor, first treated with 50 mL/min of air at 550° C. for 1 hour, and then cooled to 200° C. under a nitrogen atmosphere. Tetraethyl silicate was fed with a micro feed pump. The weight space velocity of tetraethyl silicate was 0.2 $h^{-1}$, at atmospheric pressure. After feeding for 1 hour, the feed was stopped, and after nitrogen purge, the temperature was raised to 550° C., and calcined in an air atmosphere for 4 hours. The temperature was raised to 700° C. under a nitrogen atmosphere, and the water was fed with a micro feed pump, at a water weight space velocity of 2 $h^{-1}$ and atmospheric pressure. After feeding for 4 hours, the feed was stopped to obtain a fixed bed catalyst for preparing toluene and co-producing para-xylene by alkylation from methanol and/or dimethyl ether and benzene, which was named FXCAT-25. Then, the reaction temperature was cooled to 450° C. under a nitrogen atmosphere to test the reaction of preparing toluene and co-producing para-xylene by alkylation from methanol and/or dimethyl ether and benzene. The reaction conditions were as follows: the raw materials were fed with a micro feed pump. Benzene:methanol (molar ratio) in the raw material=1:1, the total weight space velocity of benzene and methanol was 2 $h^{-1}$, at atmospheric pressure. The reaction product was analyzed by on-line Agilent 7890 gas chromatography, and the sample was anal zed at 120 min. The

TABLE 25

| Catalyst | FXCAT-25 |
| --- | --- |
| Reaction Temperature (° C.) | 450 |
| Conversion Rate of Methanol (%) | 100 |

TABLE 25-continued

| Catalyst | FXCAT-25 |
|---|---|
| Conversion Rate of Benzene (%) | 35.56 |
| Selectivity of Para-xylene in Xylene Products (wt %) | 99.82 |
| Selectivity of Para-xylene in $C_8$ Aromatic Products (wt %) | 91.40 |
| Selectivity of (Toluene + Para-xylene) in Aromatic Products (wt %) | 94.39 |
| Distribution of Products (wt %) | |
| $C_1$-$C_{6+}$ Chain Hydrocarbon | 15.31 |
| Toluene | 52.72 |
| Ethylbenzene | 2.51 |
| Para-xylene | 27.22 |
| M-xylene | 0.03 |
| O-xylene | 0.02 |
| $C_{9+}$ Aromatic Hydrocarbon | 2.19 |

Example 29: Preparation and Reaction Evaluation of Catalyst FXCAT-26 for Fixed Bed The reaction performance of on-line preparing fixed bed catalyst for preparing toluene and co-producing para-xylene by alkylation from methanol and/or dimethyl ether and benzene in a fixed bed microreactor was evaluated.

The conditions for preparing the catalyst on-line were as follows: 5 g of (40 to 60 mesh) formed molecular sieve sample FXHZSM-5-C was loaded into the fixed bed reactor, first treated with 50 mL/min of air at 550° C. for 1 hour, and then cooled to 150° C. under a nitrogen atmosphere. Tetraethyl silicate was fed with a micro feed pump. The weight space velocity of tetraethyl silicate was 0.2 $h^{-1}$, at atmospheric pressure. After feeding for 1 hour, the feed was stopped, and after nitrogen purge, the temperature was raised to 550° C., and calcined in an air atmosphere for 4 hours. The temperature was raised to 700° C. under a nitrogen atmosphere, and the water was fed with a micro feed pump, at a water weight space velocity of 2 $h^{-1}$ and atmospheric pressure. After feeding for 4 hours, the feed was stopped to obtain a fixed bed catalyst for preparing toluene and co-producing para-xylene by alkylation from methanol and/or dimethyl ether and benzene, which was named FXCAT-26. Then, the reaction temperature was cooled to 450° C. under a nitrogen atmosphere to test the reaction of preparing toluene and co-producing para-xylene by alkylation from methanol and/or dimethyl ether and benzene. The reaction conditions were as follows: the raw materials were fed with a micro feed pump. Benzene:methanol (molar ratio) in the raw material=1:1, the total weight space velocity of benzene and methanol was 2 $h^{-1}$, at atmospheric pressure. The reaction product was analyzed by on-line Agilent 7890 gas chromatography, and the sample was analyzed at 120 min. The reaction results were shown in Table 26.

TABLE 26

| Catalyst | FXCAT-26 |
|---|---|
| Reaction Temperature (° C.) | 450 |
| Conversion Rate of Methanol (%) | 100 |
| Conversion Rate of Benzene (%) | 35.87 |
| Selectivity of Para-xylene in Xylene Products (wt %) | 99.89 |
| Selectivity of Para-xylene in $C_8$ Aromatic Products (wt %) | 91.38 |
| Selectivity of (Toluene + Para-xylene) in Aromatic Products (wt %) | 94.44 |
| Distribution of Products (wt %) | |
| $C_1$-$C_{6+}$ Chain Hydrocarbon | 15.11 |
| Toluene | 52.91 |
| Ethylbenzene | 2.54 |
| Para-xylene | 27.26 |
| M-xylene | 0.02 |
| O-xylene | 0.01 |
| $C_{9+}$ Aromatic Hydrocarbon | 2.15 |

Example 30: Preparation and Reaction Evaluation of Catalyst FLCAT-27 for Fluidized Bed A fluidized bed catalyst for preparing p-toluene and co-producing para-xylene from benzene and methanol by alkylation was prepared on-line in a fixed bed reactor.

The conditions for preparing the catalyst on-line were as follows: 10 g of the formed molecular sieve sample FLHZSM-5-C was loaded into the fixed fluidized bed reactor, first treated with 50 mL/min of air at 550° C. for 1 hour, and then cooled to 200° C. under a nitrogen atmosphere. Tetraethyl silicate was fed with a micro feed pump. The weight space velocity of tetraethyl silicate was 0.2 $h^{-1}$, at atmospheric pressure. After feeding for 1 hour, the feed was stopped, and after nitrogen purge, the temperature was raised to 550° C., and calcined in an air atmosphere for 4 hours. The temperature was raised to 700° C. under a nitrogen atmosphere, and the water was fed with a micro feed pump, at a water weight space velocity of 2 $h^{-1}$ and atmospheric pressure. After feeding for 4 hours, the feed was stopped to obtain a fixed bed catalyst for preparing toluene and co-producing para-xylene by alkylation from methanol and/or dimethyl ether and benzene, which was named FLCAT-27. Then, the reaction temperature was cooled to 450° C. under a nitrogen atmosphere to test the reaction of preparing toluene and co-producing para-xylene by alkylation from methanol and/or dimethyl ether and benzene. The reaction conditions were as follows: the raw materials were fed with a micro feed pump. Benzene:methanol (molar ratio) in the raw material=1:1, the total weight space velocity of benzene and methanol was 2 $h^{-1}$, at atmospheric pressure. The reaction product was analyzed by on-line Agilent 7890 gas chromatography, and the sample was analyzed at 120 min. The reaction results were shown in Table 27.

TABLE 27

| Catalyst | FLCAT-27 |
|---|---|
| Reaction Temperature (° C.) | 450 |
| Conversion Rate of Methanol (%) | 100 |
| Conversion Rate of Benzene (%) | 32.71 |
| Selectivity of Para-xylene in Xylene Products (wt %) | 99.66 |
| Selectivity of Para-xylene in $C_8$ Aromatic Products (wt %) | 90.79 |
| Selectivity of (Toluene + Para-xylene) in Aromatic Products (wt %) | 94.03 |
| Distribution of Products (wt %) | |
| $C_1$-$C_{6+}$ Chain Hydrocarbon | 17.41 |
| Toluene | 51.05 |
| Ethylbenzene | 2.61 |
| Para-xylene | 26.61 |
| M-xylene | 0.05 |
| O-xylene | 0.04 |
| $C_{9+}$ Aromatic Hydrocarbon | 2.23 |

Example 31: Preparation and Reaction Evaluation of Catalyst FXCAT-28 for Fixed Bed The reaction performance of on-line preparing fixed bed catalyst for preparing toluene and co-producing para-xylene by alkylation from methanol and/or dimethyl ether and benzene in a fixed bed microreactor was evaluated.

The conditions for preparing the catalyst on-line were as follows: 5 g of (40 to 60 mesh) formed molecular sieve sample FXHZSM-5-C was loaded into the fixed bed reactor, first treated with 50 mL/min of air at 550° C. for 1 hour, and then cooled to 200° C. under a nitrogen atmosphere. Tetraethyl silicate was fed with a micro feed pump. The weight space velocity of tetraethyl silicate was 0.2 $h^{-1}$, at atmospheric pressure. After feeding for 1 hour, the feed was stopped, and after nitrogen purge, the temperature was raised to 550° C., and calcined in an air atmosphere for 4 hours to obtain a fixed bed catalyst for preparing toluene and co-producing para-xylene by alkylation from methanol and/or dimethyl ether and benzene, which was named FXCAT-28. Then, the reaction temperature was cooled to 450° C. under a nitrogen atmosphere to test the reaction of preparing toluene and co-producing para-xylene by alkylation from benzene and methanol. The reaction conditions were as follows: the raw materials were fed with a micro feed pump. Benzene:methanol (molar ratio) in the raw material=1:1, the total weight space velocity of benzene and methanol was 2 $h^{-1}$, at atmospheric pressure. The reaction product was analyzed by on-line Agilent 7890 gas chromatography, and the sample was analyzed at 120 min. The reaction results were shown in Table 28.

TABLE 28

| Catalyst | FXCAT-28 |
| --- | --- |
| Reaction Temperature (° C.) | 450 |
| Conversion Rate of Methanol (%) | 100 |
| Conversion Rate of Benzene (%) | 38.01 |
| Selectivity of Para-xylene in Xylene Products (wt %) | 93.60 |
| Selectivity of Para-xylene in $C_8$ Aromatic Products (wt %) | 80.64 |
| Selectivity of (Toluene + Para-xylene) in Aromatic Products (wt %) | 82.91 |
| Distribution of Products (wt %) | |
| $C_1$-$C_{6+}$ Chain Hydrocarbon | 14.06 |
| Toluene | 44.92 |
| Ethylbenzene | 4.52 |
| Para-xylene | 26.33 |
| M-xylene | 0.99 |
| O-xylene | 0.81 |
| $C_{9+}$ Aromatic Hydrocarbon | 8.37 |

Example 32: Preparation and Reaction Evaluation of Catalyst FXCAT-29 for Fixed Bed The reaction performance of on-line preparing fixed bed catalyst for preparing toluene and co-producing para-xylene and light olefins from benzene and methanol in a fixed bed microreactor was evaluated.

The conditions for preparing the catalyst on-line were as follows: 5 g of (40 to 60 mesh) formed molecular sieve sample FXHZSM-5-A was loaded into the fixed bed reactor, first treated with 50 mL/min of air at 550° C. for 1 hour, and then cooled to 200° C. under a nitrogen atmosphere. A mixture of trimethoxyphosphine and tetraethyl silicate was fed with a micro feed pump, tetraethyl silicate:trimethoxyphosphine (mass ratio)=2. The total weight space velocity of trimethoxyphosphine and tetraethyl silicate was 0.1 $h^{-1}$, at atmospheric pressure. After feeding for 1 hour, the feed was stopped, and the temperature was raised to 550° C. and calcined in an air atmosphere for 4 hours. The temperature was raised to 700° C. under a nitrogen atmosphere, and the water was fed with a micro feed pump, at a water weight space velocity of 2 $h^{-1}$ and atmospheric pressure. After feeding for 4 hours, the feed was stopped to obtain a fixed bed catalyst for preparing toluene and co-producing para-xylene and light olefins from benzene and methanol, which was named FXCAT-29. Then, the reaction temperature was cooled to 450° C. under a nitrogen atmosphere to test the reaction of preparing toluene and co-producing para-xylene and light olefins from benzene and methanol. The reaction conditions were as follows: the raw materials were fed with a micro feed pump. Benzene:methanol (molar ratio) in the raw material=1:1, the total weight space velocity of benzene and methanol was 2 $h^{-1}$, at atmospheric pressure. The reaction product was analyzed by on-line Agilent 7890 gas chromatography, and the sample was analyzed at 120 min. The reaction results were shown in Table 29.

TABLE 29

| Catalyst | FXCAT-29 |
| --- | --- |
| Reaction Temperature (° C.) | 450 |
| Conversion Rate of Methanol (%) | 100 |
| Conversion Rate of Benzene (%) | 35.51 |
| Selectivity of Para-xylene in Xylene Products (wt %) | 99.74 |
| Selectivity of Para-xylene in $C_8$ Aromatic Products (wt %) | 94.31 |
| Selectivity of (Toluene + Para-xylene) in Aromatic Products (wt %) | 95.20 |
| Distribution of Products (wt %) | |
| $C_1$-$C_{6+}$ Chain Hydrocarbon | 16.81 |
| Toluene | 52.17 |
| Ethylbenzene | 1.56 |
| Para-xylene | 27.03 |
| M-xylene | 0.04 |
| O-xylene | 0.03 |
| $C_{9+}$ Aromatic Hydrocarbon | 2.36 |
| Distribution of Hydrocarbon Products (wt %) | |
| $CH_4$ | 1.03 |
| $C_2H_4$ | 39.66 |
| $C_2H_6$ | 0.12 |
| $C_3H_6$ | 31.63 |
| $C_3H_8$ | 1.92 |
| $C_4$ | 13.43 |
| $C_5$ | 7.07 |
| $C_{6+}$ | 5.13 |
| $C_2H_4$+ $C_3H_6$ | 71.29 |

Example 33: Preparation and Reaction Evaluation of Catalyst FXCAT-30 for Fixed Bed The reaction performance of on-line preparing fixed bed catalyst for preparing toluene and co-producing para-xylene and light olefins from benzene and methanol in a fixed bed microreactor was evaluated.

The conditions for preparing the catalyst on-line were as follows: 5 g of (40 to 60 mesh) formed molecular sieve sample FXHZSM-5-A was loaded into the fixed bed reactor, first treated with 50 mL/min of air at 550° C. for 1 hour, and then cooled to 200° C. under a nitrogen atmosphere. A mixture of trimethoxyphosphine and tetraethyl silicate was fed with a micro feed pump, tetraethyl silicate:trimethoxyphosphine (mass ratio)=4. The total weight space velocity of trimethoxyphosphine and tetraethyl silicate was 0.1 $h^{-1}$, at atmospheric pressure. After feeding for 1.5 hours, the feed was stopped, and the temperature was raised to 550° C. and calcined in an air atmosphere for 4 hours. The temperature was raised to 700° C. under a nitrogen atmosphere, and the water was fed with a micro feed pump, at a water weight space velocity of 2 h$^{-1}$ and atmospheric pressure. After feeding for 4 hours, the feed was stopped to obtain a fixed bed catalyst for preparing toluene and co-producing para-xylene and light olefins from benzene and methanol, which was named FXCAT-30. Then, the reaction temperature was cooled to 450° C. under a nitrogen atmosphere to test the reaction of preparing toluene and co-producing para-xylene and light olefins from benzene and methanol. The reaction conditions were as follows: the raw materials were fed with a micro feed pump. Benzene:methanol (molar ratio) in the raw material=1:1, the total weight space velocity of benzene and methanol was 2 h$^{-1}$, at atmospheric pressure. The reaction product was analyzed by on-line Agilent 7890 gas chromatography, and the sample was analyzed at 120 min. The reaction results were shown in Table 30.

TABLE 30

| Catalyst | FXCAT-30 |
| --- | --- |
| Reaction Temperature (° C.) | 450 |
| Conversion Rate of Methanol (%) | 100 |
| Conversion Rate of Benzene (%) | 36.01 |
| Selectivity of Para-xylene in Xylene Products (wt %) | 99.66 |
| Selectivity of Para-xylene in C$_8$ Aromatic Products (wt %) | 93.24 |
| Selectivity of (Toluene + Para-xylene) in Aromatic Products (wt %) | 94.58 |
| Distribution of Products (wt %) | |
| C$_1$-C$_{6+}$ Chain Hydrocarbon | 16.57 |
| Toluene | 52.31 |
| Ethylbenzene | 1.84 |
| Para-xylene | 26.60 |
| M-xylene | 0.05 |
| O-xylene | 0.04 |
| C$_{9+}$ Aromatic Hydrocarbon | 2.59 |
| Distribution of Hydrocarbon Products (wt %) | |
| CH$_4$ | 1.12 |
| C$_2$H$_4$ | 37.13 |
| C$_2$H$_6$ | 0.16 |
| C$_3$H$_6$ | 33.02 |
| C$_3$H$_8$ | 2.17 |
| C$_4$ | 14.52 |
| C$_5$ | 7.14 |
| C$_{6+}$ | 4.74 |
| C$_2$H$_4$+ C$_3$H$_6$ | 70.15 |

Example 34: Preparation and Reaction Evaluation of Catalyst FXCAT-31 for Fixed Bed The reaction performance of on-line preparing fixed bed catalyst for preparing toluene and co-producing para-xylene and light olefins from benzene and methanol in a fixed bed microreactor was evaluated.

The conditions for preparing the catalyst on-line were as follows: 5 g of (40 to 60 mesh) formed molecular sieve sample FXHZSM-5-A was loaded into the fixed bed reactor, first treated with 50 mL/min of air at 550° C. for 1 hour, and then cooled to 200° C. under a nitrogen atmosphere. A mixture of trimethoxyphosphine and tetraethyl silicate was fed with a micro feed pump, tetraethyl silicate:trimethoxyphosphine (mass ratio)=1. The total weight space velocity of trimethoxyphosphine and tetraethyl silicate was 0.1 h$^{-1}$, at atmospheric pressure. After feeding for 1.5 hours, the feed was stopped, and the temperature was raised to 550° C. and calcined in an air atmosphere for 4 hours. The temperature was raised to 700° C. under a nitrogen atmosphere, and the water was fed with a micro feed pump, at a water weight space velocity of 2 h$^{-1}$ and atmospheric pressure. After feeding for 4 hours, the feed was stopped to obtain a fixed bed catalyst for preparing toluene and co-producing para-xylene and light olefins from benzene and methanol, which was named FXCAT-31. Then, the reaction temperature was cooled to 450° C. under a nitrogen atmosphere to test the reaction of preparing toluene and co-producing para-xylene and light olefins from benzene and methanol. The reaction conditions were as follows: the raw materials were fed with a micro feed pump. Benzene:methanol (molar ratio) in the raw material=1:1, the total weight space velocity of benzene and methanol was 2 h$^{-1}$, at atmospheric pressure. The reaction product was analyzed by on-line Agilent 7890 gas chromatography, and the sample was analyzed at 120 min. The reaction results were shown in Table 31.

TABLE 31

| Catalyst | FXCAT-31 |
| --- | --- |
| Reaction Temperature (° C.) | 450 |
| Conversion Rate of Methanol (%) | 100 |
| Conversion Rate of Benzene (%) | 33.68 |
| Selectivity of Para-xylene in Xylene Products (wt %) | 99.71 |
| Selectivity of Para-xylene in C$_8$ Aromatic Products (wt %) | 94.72 |
| Selectivity of (Toluene + Para-xylene) in Aromatic (wt %) | 95.35 |
| Distribution of Products (wt %) | |
| C$_1$-C$_{6+}$ Chain Hydrocarbon | 17.64 |
| Toluene | 51.46 |
| Ethylbenzene | 1.43 |
| Para-xylene | 27.07 |
| M-xylene | 0.04 |
| O-xylene | 0.04 |
| C$_{9+}$ Aromatic Hydrocarbon | 2.32 |
| Distribution of Hydrocarbon Products (wt %) | |
| CH$_4$ | 0.91 |
| C$_2$H$_4$ | 38.18 |
| C$_2$H$_6$ | 0.11 |
| C$_3$H$_6$ | 34 |
| C$_3$H$_8$ | 1.75 |
| C$_4$ | 12.97 |
| C$_5$ | 6.82 |
| C$_{6+}$ | 5.26 |
| C$_2$H$_4$+ C$_3$H$_6$ | 72.18 |

Example 35: Preparation and Reaction Evaluation of Catalyst FXCAT-32 for Fixed Bed The reaction performance of on-line preparing fixed bed catalyst for preparing toluene and co-producing para-xylene and light olefins from benzene and methanol in a fixed bed microreactor was evaluated.

The conditions for preparing the catalyst on-line were as follows: 5 g of (40 to 60 mesh) formed molecular sieve sample FXHZSM-5-A was loaded into the fixed bed reactor, first treated with 50 mL/min of air at 550° C. for 1 hour, and then cooled to 250° C. under a nitrogen atmosphere. A mixture of trimethoxyphosphine and tetraethyl silicate was fed with a micro feed pump, tetraethyl silicate:trimethoxyphosphine (mass ratio)=2. The total weight space velocity of trimethoxyphosphine and tetraethyl silicate was 0.1 h$^{-1}$, at atmospheric pressure. After feeding for 1 hour, the feed was stopped, and the temperature was raised to 550° C. and calcined in an air atmosphere for 4 hours. The temperature was raised to 700° C. under a nitrogen atmosphere, and the water was fed with a micro feed pump, at a water weight space velocity of 2 $h^{-1}$ and atmospheric pressure. After feeding for 4 hours, the feed was stopped to obtain a fixed bed catalyst for preparing toluene and co-producing para-xylene and light olefins from benzene and methanol, which was named FXCAT-32. Then, the reaction temperature was cooled to 450° C. under a nitrogen atmosphere to test the reaction of preparing toluene and co-producing para-xylene and light olefins from benzene and methanol. The reaction conditions were as follows: the raw materials were fed with a micro feed pump. Benzene:methanol (molar ratio) in the raw material=1:1, the total weight space velocity of benzene and methanol was 2 $h^{-1}$, at atmospheric pressure. The reaction product was analyzed by on-line Agilent 7890 gas chromatography, and the sample was analyzed at 120 min. The reaction results were shown in Table 32.

TABLE 32

| Catalyst | FXCAT-32 |
|---|---|
| Reaction Temperature (° C.) | 450 |
| Conversion Rate of Methanol (%) | 100 |
| Conversion Rate of Benzene (%) | 35.32 |
| Selectivity of Para-xylene in Xylene Products (wt %) | 99.82 |
| Selectivity of Para-xylene in $C_8$ Aromatic Products (wt %) | 94.60 |
| Selectivity of (Toluene + Para-xylene) in Aromatic Products (wt %) | 95.39 |
| Distribution of Products (wt %) | |
| $C_1$-$C_{6+}$ Chain Hydrocarbon | 17.15 |
| Toluene | 52.05 |
| Ethylbenzene | 1.49 |
| Para-xylene | 26.98 |
| M-xylene | 0.03 |
| O-xylene | 0.02 |
| $C_{9+}$ Aromatic Hydrocarbon | 2.28 |
| Distribution of Hydrocarbon Products (wt %) | |
| $CH_4$ | 0.97 |
| $C_2H_4$ | 37.92 |
| $C_2H_6$ | 0.1 |
| $C_3H_6$ | 33.95 |
| $C_3H_8$ | 1.83 |
| $C_4$ | 13.07 |
| $C_5$ | 6.93 |
| $C_{6+}$ | 5.23 |
| $C_2H_4$ + $C_3H_6$ | 71.87 |

Example 36: Preparation and Reaction Evaluation of Catalyst FXCAT-33 for Fixed Bed The reaction performance of on-line preparing fixed bed catalyst for preparing toluene and co-producing para-xylene and light olefins from benzene and methanol in a fixed bed microreactor was evaluated.

The conditions for preparing the catalyst on-line were as follows: 5 g of (40 to 60 mesh) formed molecular sieve sample FXHZSM-5-A was loaded into the fixed bed reactor, first treated with 50 mL/min of air at 550° C. for 1 hour, and then cooled to 300° C. under a nitrogen atmosphere. A mixture of trimethoxyphosphine and tetraethyl silicate was fed with a micro feed pump, tetraethyl silicate:trimethoxyphosphine (mass ratio)=2. The total weight space velocity of trimethoxyphosphine and tetraethyl silicate was 0.1 $h^{-1}$, at atmospheric pressure. After feeding for 1 hour, the feed was stopped, and the temperature was raised to 550° C. and calcined in an air atmosphere for 4 hours. The temperature was raised to 700° C. under a nitrogen atmosphere, and the water was fed with a micro feed pump, at a water weight space velocity of 2 $h^{-1}$ and atmospheric pressure. After feeding for 4 hours, the feed was stopped to obtain a fixed bed catalyst for preparing toluene and co-producing para-xylene and light olefins from benzene and methanol, which was named FXCAT-33. Then, the reaction temperature was cooled to 450° C. under a nitrogen atmosphere to test the reaction of preparing toluene and co-producing para-xylene and light olefins from benzene and methanol. The reaction conditions were as follows: the raw materials were fed with a micro feed pump. Benzene:methanol (molar ratio) in the raw material=1:1, the total weight space velocity of benzene and methanol was 2 $h^{-1}$, at atmospheric pressure. The reaction product was analyzed by on-line Agilent 7890 gas chromatography, and the sample was analyzed at 120 min. The reaction results were shown in Table 33.

TABLE 33

| Catalyst | FXCAT-33 |
|---|---|
| Reaction Temperature (° C.) | 450 |
| Conversion Rate of Methanol (%) | 100 |
| Conversion Rate of Benzene (%) | 35.95 |
| Selectivity of Para-xylene in Xylene Products (wt %) | 99.63 |
| Selectivity of Para-xylene in $C_8$ Aromatic Products (wt %) | 93.09 |
| Selectivity of (Toluene + Para-xylene) in Aromatic Products (wt %) | 94.18 |
| Distribution of Products (wt %) | |
| $C_1$-$C_{6+}$ Chain Hydrocarbon | 16.39 |
| Toluene | 51.94 |
| Ethylbenzene | 1.89 |
| Para-xylene | 26.80 |
| M-xylene | 0.06 |
| O-xylene | 0.04 |
| $C_{9+}$ Aromatic Hydrocarbon | 2.88 |
| Distribution of Hydrocarbon Products (wt %) | |
| $CH_4$ | 0.95 |
| $C_2H_4$ | 36.92 |
| $C_2H_6$ | 0.18 |
| $C_3H_6$ | 33.39 |
| $C_3H_8$ | 2.22 |
| $C_4$ | 13.57 |
| $C_5$ | 6.95 |
| $C_{6+}$ | 5.82 |
| $C_2H_4$ + $C_3H_6$ | 70.31 |

Example 37: Preparation and Reaction Evaluation of Catalyst FXCAT-34 for Fixed Bed The reaction performance of on-line preparing fixed bed catalyst for preparing toluene and co-producing para-xylene and light olefins from benzene and methanol in a fixed bed microreactor was evaluated.

The conditions for preparing the catalyst on-line were as follows: 5 g of (40 to 60 mesh) formed molecular sieve sample FXHZSM-5-A was loaded into the fixed bed reactor, first treated with 50 mL/min of air at 550° C. for 1 hour, and then cooled to 200° C. under a nitrogen atmosphere. A mixture of trimethoxyphosphine and tetraethyl silicate was fed with a micro feed pump, tetraethyl silicate:trimethoxyphosphine (mass ratio)=2. The total weight space velocity of trimethoxyphosphine and tetraethyl silicate was 0.1 $h^{-1}$, at atmospheric pressure. After feeding for 1 hour, the feed was stopped, and the temperature was raised to 550° C. and calcined in an air atmosphere for 4 hours. The temperature was raised to 800° C. under a nitrogen atmosphere, and the water was fed with a micro feed pump, at a water weight space velocity of 2 $h^{-1}$ and atmospheric pressure. After feeding for 2 hours, the feed was stopped to obtain a fixed bed catalyst for preparing toluene and co-producing para-xylene and light olefins from benzene and methanol, which was named FXCAT-34. Then, the reaction temperature was cooled to 450° C. under a nitrogen atmosphere to test the reaction of preparing toluene and co-producing para-xylene and light olefins from benzene and methanol. The reaction conditions were as follows: the raw materials were fed with a micro feed pump. Benzene:methanol (molar ratio) in the raw material=1:1, the total weight space velocity of benzene and methanol was 2 $h^{-1}$, at atmospheric pressure. The reaction product was analyzed by on-line Agilent 7890 gas chromatography, and the sample was analyzed at 120 min. The reaction results were shown in Table 34.

TABLE 34

| Catalyst | FXCAT-34 |
|---|---|
| Reaction Temperature (° C.) | 450 |
| Conversion Rate of Methanol (%) | 100 |
| Conversion Rate of Benzene (%) | 32.17 |
| Selectivity of Para-xylene in Xylene Products (wt %) | 99.88 |
| Selectivity of Para-xylene in $C_8$ Aromatic Products (wt %) | 94.69 |
| Selectivity of (Toluene + Para-xylene) in Aromatic Products (wt %) | 95.50 |
| Distribution of Products (wt %) | |
| $C_1$-$C_{6+}$ Chain Hydrocarbon | 18.23 |
| Toluene | 52.05 |
| Ethylbenzene | 1.43 |
| Para-xylene | 26.04 |
| M-xylene | 0.02 |
| O-xylene | 0.01 |
| $C_{9+}$ Aromatic Hydrocarbon | 2.22 |
| Distribution of Hydrocarbon Products (wt %) | |
| $CH_4$ | 1.09 |
| $C_2H_4$ | 39.52 |
| $C_2H_6$ | 0.11 |
| $C_3H_6$ | 32.09 |
| $C_3H_8$ | 1.83 |
| $C_4$ | 13.19 |
| $C_5$ | 6.95 |
| $C_{6+}$ | 5.22 |
| $C_2H_4$ + $C_3H_6$ | 71.61 |

Example 38: Preparation and Reaction Evaluation of Catalyst FXCAT-35 for Fixed Bed The reaction performance of on-line preparing fixed bed catalyst for preparing toluene and co-producing para-xylene and light olefins from benzene and methanol in a fixed bed microreactor was evaluated.

The conditions for preparing the catalyst on-line were as follows: 5 g of (40 to 60 mesh) formed molecular sieve sample FXHZSM-5-A was loaded into the fixed bed reactor, first treated with 50 mL/min of air at 550° C. for 1 hour, and then cooled to 200° C. under a nitrogen atmosphere. A mixture of trimethoxyphosphine and tetraethyl silicate was fed with a micro feed pump, tetraethyl silicate:trimethoxyphosphine (mass ratio)=2. The total weight space velocity of trimethoxyphosphine and tetraethyl silicate was 0.1 $h^{-1}$, at atmospheric pressure. After feeding for 1 hour, the feed was stopped, and calcined in an air atmosphere for 4 hours. The temperature was raised to 600° C. under a nitrogen atmosphere, and the water was fed with a micro feed pump, at a water weight space velocity of 2 $h^{-1}$ and atmospheric pressure. After feeding for 8 hours, the feed was stopped to obtain a fixed bed catalyst for preparing toluene and co-producing para-xylene and light olefins from benzene and methanol, which was named FXCAT-35. Then, the reaction temperature was cooled to 450° C. under a nitrogen atmosphere to test the reaction of preparing toluene and co-producing para-xylene and light olefins from benzene and methanol. The reaction conditions were as follows: the raw materials were fed with a micro feed pump. Benzene:methanol (molar ratio) in the raw material=1:1, the total weight space velocity of benzene and methanol was 2 $h^{-1}$, at atmospheric pressure. The reaction product was analyzed by on-line Agilent 7890 gas chromatography, and the sample was analyzed at 120 min. The reaction results were shown in Table 35.

TABLE 35

| Catalyst | FXCAT-35 |
|---|---|
| Reaction Temperature (° C.) | 450 |
| Conversion Rate of Methanol (%) | 100 |
| Conversion Rate of Benzene (%) | 35.59 |
| Selectivity of Para-xylene in Xylene Products (wt %) | 99.74 |
| Selectivity of Para-xylene in $C_8$ Aromatic Products (wt %) | 94.23 |
| Selectivity of (Toluene + Para-xylene) in Aromatic Products (wt %) | 95.07 |
| Distribution of Products (wt %) | |
| $C_1$-$C_{6+}$ Chain Hydrocarbon | 16.15 |
| Toluene | 52.94 |
| Ethylbenzene | 1.57 |
| Para-xylene | 26.78 |
| M-xylene | 0.04 |
| O-xylene | 0.03 |
| $C_{9+}$ Aromatic Hydrocarbon | 2.49 |
| Distribution of Hydrocarbon Products (wt %) | |
| $CH_4$ | 1.01 |
| $C_2H_4$ | 39.25 |
| $C_2H_6$ | 0.13 |
| $C_3H_6$ | 31.55 |
| $C_3H_8$ | 1.93 |
| $C_4$ | 13.51 |
| $C_5$ | 7.27 |
| $C_{6+}$ | 5.35 |
| $C_2H_4$ + $C_3H_6$ | 70.80 |

Example 39: Preparation and Reaction Evaluation of Catalyst FXCAT-36 for Fixed Bed The reaction performance of on-line preparing fixed bed catalyst for preparing toluene and co-producing para-xylene and light olefins from benzene and methanol in a fixed bed microreactor was evaluated.

The conditions for preparing the catalyst on-line were as follows: 5 g of (40 to 60 mesh) formed molecular sieve sample FXHZSM-11-A catalyst was tabletted and crushed into 40-60 mesh, 5 g of (40 to 60 mesh) catalyst was loaded into the fixed bed reactor, first treated with 50 mL/min of air at 550° C. for 1 hour, and then cooled to 200° C. under a nitrogen atmosphere. A mixture of trimethoxyphosphine and tetraethyl silicate was fed with a micro feed pump, tetraethyl silicate:trimethoxyphosphine (mass ratio)=2. The total weight space velocity of trimethoxyphosphine and tetraethyl silicate was 0.1 $h^{-1}$, at atmospheric pressure. After feeding for 1 hour, the feed was stopped, and the temperature was raised to 550° C. and calcined in an air atmosphere for 4 hours. The temperature was raised to 700° C. under a nitrogen atmosphere, and the water was fed with a micro feed pump, at a water weight space velocity of 2 h$^{-1}$ and atmospheric pressure. After feeding for 4 hours, the feed was stopped to obtain a fixed bed catalyst for preparing toluene and co-producing para-xylene and light olefins from benzene and methanol, which was named FXCAT-36. Then, the reaction temperature was cooled to 450° C. under a nitrogen atmosphere to test the reaction of preparing toluene and co-producing para-xylene and light olefins from benzene and methanol. The reaction conditions were as follows: the raw materials were fed with a micro feed pump. Benzene: methanol (molar ratio) in the raw material=1:1, the total weight space velocity of benzene and methanol was 2 h$^{-1}$, at atmospheric pressure. The reaction product was analyzed by on-line Agilent 7890 gas chromatography, and the sample was analyzed at 120 min. The reaction results were shown in Table 36.

TABLE 36

| Catalyst | FXCAT-36 |
| --- | --- |
| Reaction Temperature (° C.) | 450 |
| Conversion Rate of Methanol (%) | 100 |
| Conversion Rate of Benzene (%) | 34.17 |
| Selectivity of Para-xylene in Xylene Products (wt %) | 99.85 |
| Selectivity of Para-xylene in C$_8$ Aromatic Products (wt %) | 94.49 |
| Selectivity of (Toluene + Para-xylene) in Aromatic Products (wt %) | 95.46 |
| Distribution of Products (wt %) | |
| C$_1$-C$_{6+}$ Chain Hydrocarbon | 18.13 |
| Toluene | 51.89 |
| Ethylbenzene | 1.49 |
| Para-xylene | 26.26 |
| M-xylene | 0.03 |
| O-xylene | 0.01 |
| C$_{9+}$ Aromatic Hydrocarbon | 2.19 |
| Distribution of Hydrocarbon Products (wt %) | |
| CH$_4$ | 0.91 |
| C$_2$H$_4$ | 38.61 |
| C$_2$H$_6$ | 0.09 |
| C$_3$H$_6$ | 34.07 |
| C$_3$H$_8$ | 1.6 |
| C$_4$ | 12.23 |
| C$_5$ | 6.85 |
| C$_{6+}$ | 5.64 |
| C$_2$H$_4$+ C$_3$H$_6$ | 72.68 |

Example 40: Preparation and Reaction Evaluation of Catalyst FXCAT-37 for Fixed Bed The reaction performance of on-line preparing fixed bed catalyst for preparing toluene and co-producing para-xylene and light olefins from benzene and methanol in a fixed bed microreactor was evaluated.

The conditions for preparing the catalyst on-line were as follows: 5 g of (40 to 60 mesh) formed molecular sieve sample FXHZSM-5-A was loaded into the fixed bed reactor, first treated with 50 mL/min of air at 550° C. for 1 hour, and then cooled to 200° C. under a nitrogen atmosphere. A mixture of trimethoxyphosphine and tetraethyl silicate was fed with a micro feed pump, tetraethyl silicate:trimethoxyphosphine (mass ratio)=2. The total weight space velocity of trimethoxyphosphine and tetraethyl silicate was 0.1 h$^{-1}$, at atmospheric pressure. After feeding for 1 hour, the feed was stopped, and the temperature was raised to 550° C. and calcined in an air atmosphere for 4 hours. The temperature was raised to 700° C. under a nitrogen atmosphere, and the water was fed with a micro feed pump, at a water weight space velocity of 2 h$^{-1}$ and atmospheric pressure. After feeding for 4 hours, the feed was stopped to obtain a fixed bed catalyst for preparing toluene and co-producing para-xylene and light olefins from benzene and methanol, which was named FXCAT-37. Then, the reaction temperature was cooled to 450° C. under a nitrogen atmosphere to test the reaction of preparing toluene and co-producing para-xylene and light olefins from benzene and methanol. The reaction conditions were as follows: the raw materials were fed with a micro feed pump. Benzene:methanol (molar ratio) in the raw material=1:1, the total weight space velocity of benzene and methanol was 2 h$^{-1}$, at atmospheric pressure. The reaction product was analyzed by on-line Agilent 7890 gas chromatography, and the sample was analyzed at 120 min. The reaction results were shown in Table 37.

TABLE 37

| Catalyst | FXCAT-37 |
| --- | --- |
| Reaction Temperature (° C.) | 450 |
| Conversion Rate of Methanol (%) | 100 |
| Conversion Rate of Benzene (%) | 33.86 |
| Selectivity of Para-xylene in Xylene Products (wt %) | 99.85 |
| Selectivity of Para-xylene in C$_8$ Aromatic Products (wt %) | 94.59 |
| Selectivity of (Toluene + Para-xylene) in Aromatic Products (wt %) | 95.51 |
| Distribution of Products (wt %) | |
| C$_1$-C$_{6+}$ Chain Hydrocarbon | 18.67 |
| Toluene | 51.46 |
| Ethylbenzene | 1.46 |
| Para-xylene | 26.22 |
| M-xylene | 0.02 |
| O-xylene | 0.02 |
| C$_{9+}$ Aromatic Hydrocarbon | 2.15 |
| Distribution of Hydrocarbon Products (wt %) | |
| CH$_4$ | 1.05 |
| C$_2$H$_4$ | 37.59 |
| C$_2$H$_6$ | 0.1 |
| C$_3$H$_6$ | 34.03 |
| C$_3$H$_8$ | 1.69 |
| C$_4$ | 13.02 |
| C$_5$ | 6.77 |
| C$_{6+}$ | 5.75 |
| C$_2$H$_4$+ C$_3$H$_6$ | 71.62 |

Example 41: Preparation and Reaction Evaluation of Catalyst FLCAT-38 for Fluidized Bed A fluidized bed catalyst for preparing toluene and co-producing para-xylene and light olefins from benzene and methanol was prepared on-line in a fixed bed reactor.

The conditions for preparing the catalyst on-line were as follows: 10 g of the formed molecular sieve sample FLHZSM-5-A was loaded into the fixed fluidized bed reactor, first treated with 50 mL/min of air at 550° C. for 1 hour, and then cooled to 200° C. under a nitrogen atmosphere. A mixture of trimethoxyphosphine and tetraethyl silicate was fed with a micro feed pump, tetraethyl silicate:trimethoxyphosphine (mass ratio)=2. The total weight space velocity of trimethoxyphosphine and tetraethyl silicate was 0.1 h$^{-1}$, at atmospheric pressure. After feeding for 1 hour, the feed was stopped, and the temperature was raised to 550° C. and calcined in an air atmosphere for 4 hours. The temperature was raised to 700° C. under a nitrogen atmosphere, and the water was fed with a micro feed pump, at a water weight space velocity of 2 h$^{-1}$ and atmospheric pressure. After feeding for 4 hours, the feed was stopped to obtain a fluidized bed catalyst for preparing toluene and co-producing para-xylene and light olefins from benzene and methanol, which was named FLCAT-38. Then, the reaction temperature was cooled to 450° C. under a nitrogen atmosphere to test the reaction of preparing toluene and co-producing para-xylene and light olefins from methanol and/or dimethyl ether and benzene by alkylation. The reaction conditions were as follows: the raw materials were fed with a micro feed pump. Benzene:methanol (molar ratio) in the raw material=1:1, the total weight space velocity of benzene and methanol was 2 $h^{-1}$, at atmospheric pressure. The reaction product was analyzed by on-line Agilent 7890 gas chromatography, and the sample was analyzed at 120 min. The reaction results were shown in Table 38.

TABLE 38

| Catalyst | FLCAT-38 |
|---|---|
| Reaction Temperature (° C.) | 450 |
| Conversion Rate of Methanol (%) | 100 |
| Conversion Rate of Benzene (%) | 30.18 |
| Selectivity of Para-xylene in Xylene Products (wt %) | 99.70 |
| Selectivity of Para-xylene in $C_8$ Aromatic Products (wt %) | 93.30 |
| Selectivity of (Toluene + Para-xylene) in Aromatic Products (wt %) | 94.56 |
| Distribution of Products (wt %) | |
| $C_1$-$C_{6+}$ Chain Hydrocarbon | 17.43 |
| Toluene | 51.48 |
| Ethylbenzene | 1.83 |
| Para-xylene | 26.60 |
| M-xylene | 0.05 |
| O-xylene | 0.03 |
| $C_{9+}$ Aromatic Hydrocarbon | 2.58 |
| Distribution of Hydrocarbon Products (wt %) | |
| $CH_4$ | 1.01 |
| $C_2H_4$ | 36.73 |
| $C_2H_6$ | 0.11 |
| $C_3H_6$ | 34.09 |
| $C_3H_8$ | 1.93 |
| $C_4$ | 13.55 |
| $C_5$ | 7.20 |
| $C_{6+}$ | 5.38 |
| $C_2H_4$+ $C_3H_6$ | 70.82 |

Example 42: Preparation and Reaction Evaluation of Catalyst FXCAT-39 for Fixed Bed The reaction performance of on-line preparing fixed bed catalyst for preparing toluene and co-producing para-xylene and light olefins from benzene and methanol in a fixed bed microreactor was evaluated.

The conditions for preparing the catalyst on-line were as follows: 5 g of (40 to 60 mesh) formed molecular sieve sample FXHZSM-5-A was loaded into the fixed bed reactor, first treated with 50 mL/min of air at 550° C. for 1 hour, and then cooled to 200° C. under a nitrogen atmosphere. A mixture of trimethoxyphosphine and tetraethyl silicate was fed with a micro feed pump, tetraethyl silicate:trimethoxyphosphine (mass ratio)=2. The total weight space velocity of trimethoxyphosphine and tetraethyl silicate was 0.1 $h^{-1}$, at atmospheric pressure. After feeding for 1 hour, the feed was stopped, and after nitrogen purge, the temperature was raised to 550° C., and calcined in an air atmosphere for 4 hours to obtain a fixed bed catalyst for preparing toluene and co-producing para-xylene and light olefins from benzene and methanol, which was named FXCAT-39. Then, the reaction temperature was cooled to 450° C. under a nitrogen atmosphere to test the reaction of preparing toluene and co-producing para-xylene and light olefins from benzene and methanol. The reaction conditions were as follows: the raw materials were fed with a micro feed pump. Benzene: methanol (molar ratio) in the raw material=1:1, the total weight space velocity of benzene and methanol was 2 $h^{-1}$, at atmospheric pressure. The reaction product was analyzed by on-line Agilent 7890 gas chromatography, and the sample was analyzed at 120 min. The reaction results were shown in Table 39.

TABLE 39

| Catalyst | FXCAT-39 |
|---|---|
| Reaction Temperature (° C.) | 450 |
| Conversion Rate of Methanol (%) | 100 |
| Conversion Rate of Benzene (%) | 37.97 |
| Selectivity of Para-xylene in Xylene Products (wt %) | 95.28 |
| Selectivity of Para-xylene in $C_8$ Aromatic Products (wt %) | 83.25 |
| Selectivity of (Toluene + Para-xylene) in Aromatic Products (wt %) | 88.45 |
| Distribution of Products (wt %) | |
| $C_1$-$C_{6+}$ Chain Hydrocarbon | 15.91 |
| Toluene | 48.53 |
| Ethylbenzene | 3.92 |
| Para-xylene | 25.85 |
| M-xylene | 0.71 |
| O-xylene | 0.57 |
| $C_{9+}$ Aromatic Hydrocarbon | 4.51 |
| Distribution of Chain Hydrocarbon Products (wt %) | |
| $CH_4$ | 0.98 |
| $C_2H_4$ | 33.21 |
| $C_2H_6$ | 0.23 |
| $C_3H_6$ | 31.15 |
| $C_3H_8$ | 2.62 |
| $C_4$ | 16.99 |
| $C_5$ | 8.94 |
| $C_{6+}$ | 5.88 |
| $C_2H_4$+ $C_3H_6$ | 64.36 |

Example 43: Preparation and Reaction Evaluation of Catalyst FXCAT-40 for Fixed Bed The reaction performance of on-line preparing fixed bed catalyst for preparing toluene and co-producing para-xylene and light olefins from benzene and methanol in a fixed bed microreactor was evaluated.

The conditions for preparing the catalyst on-line were as follows: 5 g of (40 to 60 mesh) formed molecular sieve sample FXHZSM-5-A was loaded into the fixed bed reactor, first treated with 50 mL/min of air at 550° C. for 1 hour, and then cooled to 200° C. under a nitrogen atmosphere. Tetraethyl silicate was fed with a micro feed pump. The weight space velocity of tetraethyl silicate was 0.067 $h^{-1}$, at atmospheric pressure. After feeding for 1 hour, the feed was stopped, and after nitrogen purge, the temperature was raised to 550° C., and calcined in an air atmosphere for 4 hours. The temperature was raised to 700° C. under a nitrogen atmosphere, and the water was fed with a micro feed pump, at a water weight space velocity of 2 $h^{-1}$ and atmospheric pressure. After feeding for 4 hours, the feed was stopped to obtain a fixed bed catalyst for preparing toluene and co-producing para-xylene and light olefins from benzene and methanol, which was named FXCAT-40. Then, the reaction temperature was cooled to 450° C. under a nitrogen atmosphere to test the reaction of preparing toluene and co-producing para-xylene and light olefins from benzene and methanol. The reaction conditions were as follows: the raw materials were fed with a micro feed pump. Benzene:methanol (molar ratio) in the raw material=1:1, the total weight space velocity of benzene and methanol was 2 $h^{-1}$, at atmospheric pressure. The reaction product was analyzed by on-line Agilent 7890 gas chromatography, and the sample was analyzed at 120 min. The reaction results were shown in Table 40.

TABLE 40

| Catalyst | FXCAT-40 |
|---|---|
| Reaction Temperature (° C.) | 450 |
| Conversion Rate of Methanol (%) | 100 |
| Conversion Rate of Toluene (%) | 35.93 |
| Selectivity of Para-xylene in Xylene Products (wt %) | 99.49 |
| Selectivity of Para-xylene in $C_8$ Aromatic Products (wt %) | 90.93 |
| Selectivity of (Toluene + Para-xylene) in Aromatic Products (wt %) | 94.11 |
| Distribution of Products (wt %) | |
| $C_1$-$C_{6+}$ Chain Hydrocarbon | 14.72 |
| Toluene | 53.09 |
| Ethylbenzene | 2.57 |
| Para-xylene | 27.17 |
| M-xylene | 0.09 |
| O-xylene | 0.05 |
| $C_{9+}$ Aromatic Hydrocarbon | 2.31 |
| Distribution of Chain Hydrocarbon Products (wt %) | |
| $CH_4$ | 1.31 |
| $C_2H_4$ | 11.73 |
| $C_2H_6$ | 0.98 |
| $C_3H_6$ | 20.65 |
| $C_3H_8$ | 11.31 |
| $C_4$ | 29.13 |
| $C_5$ | 14.86 |
| $C_{6+}$ | 10.03 |
| $C_2H_4$+ $C_3H_6$ | 32.38 |

Example 44: Preparation and Reaction Evaluation of Catalyst FXCAT-41 for Fixed Bed The apparatus, operation and conditions were the same as those in Example 5 except that the trimethoxyphosphine was replaced with methyldiethoxyphosphine, during the preparation of the catalyst, and the others were unchanged to prepare the fixed bed catalyst for preparing light olefins and co-producing para-xylene from methanol and toluene, which was named FXCAT-41. The reaction evaluation conditions were the same as in Example 5, the reaction results were consistent with Example 5 (the deviation was not more than ±1%).

Example 45: Preparation and Reaction Evaluation of Catalyst FLCAT-42 for Fluidized Bed The reaction performance of on-line preparing fluidized bed catalyst for preparing para-xylene from toluene and methanol by alkylation in a fixed fluidized bed reactor was evaluated.

The conditions for preparing the catalyst on-line were as follows: 1 kg of the formed molecular sieve sample FLHZSM-5-B was loaded into the fixed fluidized bed reactor at the reactor temperature of 300° C., the content of tetraethyl silicate in a mixture of tetraethyl silicate, toluene and methanol was 10% by weight, and toluene:methanol (molar ratio)=2:1, and the total weight space velocity of a mixture of tetraethyl silicate, toluene and methanol was 2 $h^{-1}$. After feeding for 10 hours, the feed was stopped to obtain the catalyst for preparing para-xylene from toluene and methanol by alkylation, which was named FLCAT-42.

After preparing FLCAT-42 on-line, it was switched to toluene and methanol alkylation reaction. The reaction conditions were as follows: at the reaction temperature of 450° C., toluene:methanol (molar ratio) in the raw material=2:1, the total weight space velocity of toluene and methanol was 2 $h^{-1}$, at atmospheric pressure. The reaction product was analyzed by on-line Agilent 7890 gas chromatography. The reaction results were shown in Table 41.

TABLE 41

| Catalyst | FLCAT-42 |
|---|---|
| Reaction Temperature (° C.) | 450 |
| Feeding Time (min) | 120 |
| Conversion Rate of Methanol (%) | 100 |
| Conversion Rate of Benzene (%) | 27.15 |
| Selectivity of Para-xylene in Xylene Products (wt %) | 95.08 |
| Distribution of Products (wt %) | |
| $C_1$-$C_{6+}$ Chain Hydrocarbon | 17.22 |
| Benzene | 0.51 |
| Ethylbenzene | 0.18 |
| Para-xylene | 73.85 |
| M-xylene | 2.03 |
| O-xylene | 1.79 |
| $C_{9+}$ Aromatic Hydrocarbon | 4.42 |

The above description is only a few embodiments of the present application, and is not intended to limit the application in any way. While the present application has been described above with reference to preferred embodiments, but these embodiments are not intended to limit the present application. Without departing from the spirit of the present application, one skilled in the art will be able to make several possible variations and modifications and thus the protection scope shall be determined by the scope as defined in the claims.

What is claimed is:

1. A method for carrying out Reaction I, wherein a raw material comprising methanol and/or dimethyl ether and toluene is contacted with a catalyst obtained by an in-situ and on-line preparation method in a reactor to prepare light olefins and co-produce para-xylene;

Reaction I is to prepare light olefins from methanol and/or dimethyl ether and toluene and co-produce para-xylene;

wherein; a material stream I is contacted with the catalyst in a reaction system to obtain a material stream II, a $C_4$ olefin or a $C_{5+}$ chain hydrocarbon is separated from the material stream II and returned to the reaction system, and light olefins and para-xylene separated from the material stream II are used as products;

the material stream I comprises methanol and/or dimethyl ether and toluene;

wherein the reaction system comprises:

a first reaction zone containing a Catalyst A; and a second reaction zone containing a Catalyst B; and wherein the Catalyst A is a HZSM-5 molecular sieve catalyst modified by a phosphorus reagent and a silylation reagent, the specific preparation steps are as follows:

(A1) a mixture of the phosphorus reagent, the silylation reagent and toluene is fed into the first reaction zone with the HZSM-5 molecular sieve at the temperature ranging from 130° C. to 500° C.; and (A2) the temperature is raised to above 500° C., and calcined in an air atmosphere for a period of time ranging from 1 hour to 6 hours to obtain the Catalyst A; and wherein the Catalyst B is a HZSM-5 molecular sieve catalyst modified by a silylation reagent, the specific preparation steps are as follows:

(B1) a mixture of the silylation reagent and methanol is fed into the second reaction zone with the HZSM-5 molecular sieve at the temperature ranging from 120° C. to 250° C.; and (B2) the temperature is raised to above 500° C., and calcined in an air atmosphere for a period of time ranging from 1 hour to 6 hours to obtain the Catalyst B.

2. The method of claim 1, wherein the raw material is contacted with the catalyst at a reaction temperature ranging from 350° C. to 650° C.;

in the raw material containing methanol and/or dimethyl ether and toluene, the ratio of methanol and/or dimethyl ether to toluene is as follows:

the number of carbon atoms of methanol and dimethyl ether: moles of toluene=0.5 to 10.

3. The method of claim 1, wherein the phosphorus reagent is selected from compounds having the following formula (I):

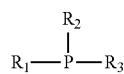
(I)

$R_1$, $R_2$ and $R_3$ are independently selected from $C_{1-10}$ alkyl and $C_{1-10}$ alkoxy, wherein the phosphorus reagent is at least one selected from trimethoxyphosphine, triethoxyphosphine, tripropoxyphosphine, tributoxyphosphine and methyldiethoxyphosphine.

4. The method of claim 3, wherein at least one of $R_1$, $R_2$ and $R_3$ in the formula (I) is selected from $C_{1-10}$ alkoxy.

5. The method of claim 3, wherein the phosphorus reagent is at least one selected from trimethoxyphosphine, triethoxyphosphine, tripropoxyphosphine, tributoxyphosphine and methyldiethoxyphosphine.

6. The method of claim 1, wherein the material stream I is contacted with the catalyst in the first reaction zone to obtain a material stream II-A, the material stream II-A is fed to a separation system and the $C_4$ olefin or the $C_{5+}$ chain hydrocarbon, light olefins and para-xylene are separated;

the $C_4$ olefin or the $C_{5+}$ chain hydrocarbon separated in the separation system is fed into the second reaction zone to contact the catalyst to obtain a material stream II-B, the material stream II-B is fed into the separation system; and light olefins and para-xylene separated in the separation system are used as products.

7. The method of claim 1, wherein the reaction system comprises one reactor or a plurality of reactors connected by series and/or parallel;

the reactor is at least one of a fixed bed reactor, a fluidized bed reactor or a moving bed reactor.

8. The method of claim 1, wherein the first reaction zone comprises one reactor or a plurality of reactors connected by series and/or parallel, and the second reaction zone comprises one reactor or a plurality of reactors connected by series and/or parallel;

the total weight space velocity of the raw material is in a range from 0.1 $h^{-1}$ to 10 $h^{-1}$.

9. The method of claim 8, wherein the total weight space velocity of the raw material is in a range from 0.8 $h^{-1}$ to 3 $h^{-1}$.

10. The method of claim 8, wherein the molar content of toluene in the raw material is in a range from 5 mol % to 50 mol %.

11. The method of claim 1, wherein the silylation reagent is at least one selected from the compounds having the following formula (II):

(II)

$R_4$, $R_5$, $R_6$ and $R_7$ are independently selected from $C_{1-10}$ alkyl and $C_{1-10}$ alkoxy.

12. The method of claim 11, wherein at least one of $R_4$, $R_5$, $R_6$ and $R_7$ in the formula (II) is selected from $C_{1-10}$ alkoxy.

13. The method of claim 11, wherein the silylation reagent is at least one selected from tetramethyl silicate, tetraethyl silicate, tetrapropyl silicate and tetrabutyl silicate.

* * * * *